(12) United States Patent
McSpadden et al.

(10) Patent No.: US 10,183,268 B1
(45) Date of Patent: *Jan. 22, 2019

(54) METHOD OF MANUFACTURING BIO-DIESEL AND REACTOR

(71) Applicant: Louisiana Eco Green, L.L.C., Golden Meadow, LA (US)

(72) Inventors: Kemper J. McSpadden, Golden Meadow, LA (US); Gerard M. Thomassie, Golden Meadow, LA (US)

(73) Assignee: Louisiana Eco Green, LLC, Golden Meadow, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/331,586

(22) Filed: Oct. 21, 2016

Related U.S. Application Data

(63) Continuation of application No. 14/012,810, filed on Aug. 28, 2013, now Pat. No. 9,475,029.

(51) Int. Cl.
| | | |
|---|---|---|
| *B01J 19/00* | (2006.01) | |
| *B01J 19/24* | (2006.01) | |
| *C10L 1/02* | (2006.01) | |
| *C07C 67/08* | (2006.01) | |
| *C07C 67/03* | (2006.01) | |

(52) U.S. Cl.
CPC ............ *B01J 19/24* (2013.01); *B01J 19/242* (2013.01); *B01J 19/243* (2013.01); *B01J 19/2425* (2013.01); *C07C 67/03* (2013.01); *C07C 67/08* (2013.01); *C10L 1/026* (2013.01); *B01J 2219/00083* (2013.01); *B01J 2219/00085* (2013.01); *B01J 2219/00087* (2013.01); *B01J 2219/00099* (2013.01);

(Continued)

(58) Field of Classification Search
CPC .... B01J 19/242; B01J 19/2425; B01J 19/243; B01J 19/24; B01J 19/2405; B01J 19/2415; B01J 2219/00099; B01J 3/042; B01J 3/044

See application file for complete search history.

(56) References Cited

U.S. PATENT DOCUMENTS

| | | |
|---|---|---|
| 1,213,143 A | 1/1917 | Aylsworth |
| 3,929,421 A | 12/1975 | Werges |

(Continued)

OTHER PUBLICATIONS

Dadan Kusdiana, Shiro Saka, "Effects of Water on Biodiesel Fuel Production by Supercritical Methanol Treatment", 2004, Bioresource Technology, 91, 289-295.

*Primary Examiner* — Lessanework Seifu
(74) *Attorney, Agent, or Firm* — Roy Kiesel Ford Doody & Thurmon APLC

(57) ABSTRACT

A reactor and process for the production of bio-diesel. The reactor includes one or more coiled reaction lines. The lines are positioned within a tank containing a heat transfer media such as molten salt, maintained at about 750° F. A pump circulates the media within the tank. An emulsion of alcohol; refined feed stock, including glycerides and/or fatty acids; and preferably water is pumped through the reaction lines at temperatures and pressures sufficient to maintain the alcohol in a super-critical state. The curvature of the coils, pump pulsing, and the flow rate of the emulsion keep the emulsion in a turbulent state while in the reactor, ensuring thorough mixing of the alcohol and feed stock. The alcohol reacts with the glycerides and fatty acids to form bio-diesel. The reaction is fast, efficient with regard to energy input and waste generation, and requires minimal alcohol.

27 Claims, 12 Drawing Sheets

(52) U.S. Cl.
CPC .. *B01J 2219/185* (2013.01); *B01J 2219/1943* (2013.01); *C10L 2200/0469* (2013.01); *C10L 2290/06* (2013.01)

(56) References Cited

U.S. PATENT DOCUMENTS

| | | | |
|---|---|---|---|
| 5,843,386 A | 12/1998 | Makino et al. | |
| 5,932,182 A | 8/1999 | Blaney | |
| 6,818,026 B2 | 11/2004 | Tateno | |
| 6,960,672 B2 | 11/2005 | Nakayama | |
| 6,979,426 B2 | 12/2005 | Teall | |
| 7,161,017 B2 | 1/2007 | Garro | |
| 7,227,030 B2 | 6/2007 | Saka | |
| 7,247,739 B2 | 7/2007 | Gapes | |
| 7,524,982 B2 | 4/2009 | Dall'Agnol | |
| 7,547,539 B2 | 6/2009 | Ikegami | |
| 7,638,068 B1 | 12/2009 | Toombs | |
| 7,638,314 B2 | 12/2009 | Zappi | |
| 7,691,270 B2 | 4/2010 | Ginosar | |
| 7,718,698 B2 | 5/2010 | Breivik | |
| 7,732,488 B2 | 6/2010 | Breivik | |
| 7,772,414 B1 | 8/2010 | Hybertson | |
| 7,781,619 B2 | 8/2010 | Brevoord | |
| 7,897,798 B2 | 3/2011 | McNeff | |
| 7,943,791 B2 | 5/2011 | McNeff | |
| 7,955,508 B2 | 6/2011 | Allan | |
| 7,988,927 B2 | 8/2011 | Lehr et al. | |
| 8,017,796 B2 | 9/2011 | McNeff | |
| 8,066,785 B2 | 11/2011 | Gonchar | |
| 8,067,624 B2 | 11/2011 | Elst | |
| 8,076,498 B2 | 12/2011 | Elst et al. | |
| 8,148,559 B1 | 4/2012 | Walker | |
| 8,178,326 B2 | 5/2012 | Greyt | |
| 8,188,305 B2 | 5/2012 | Miller | |
| 8,227,632 B2 | 7/2012 | Berry | |
| 8,288,573 B2 | 10/2012 | Wang | |
| 8,304,566 B2 | 11/2012 | Cantizani | |
| 8,309,783 B2 | 11/2012 | Strege | |
| 8,323,501 B2 | 12/2012 | Kale | |
| 8,329,036 B2 | 12/2012 | Kale | |
| 8,592,613 B2 | 11/2013 | Berry et al. | |
| 9,329,449 B2 | 5/2016 | Qin | |
| 9,475,029 B2 | 10/2016 | McSpadden et al. | |
| 2002/0182128 A1 | 12/2002 | Carhahan et al. | |
| 2003/0032826 A1 | 2/2003 | Hanna | |
| 2005/0274065 A1 | 12/2005 | Portnoff et al. | |
| 2006/0288636 A1 | 12/2006 | Iijima | |
| 2007/0175092 A1 | 8/2007 | Ames | |
| 2008/0023175 A1 | 1/2008 | Lehr et al. | |
| 2008/0282606 A1 | 11/2008 | Plaza et al. | |
| 2009/0005582 A1 | 1/2009 | Anderson | |
| 2011/0232161 A1 | 9/2011 | Siskin et al. | |
| 2011/0319651 A1 | 12/2011 | Maeda et al. | |
| 2015/0027036 A1 | 1/2015 | Janajreh | |
| 2015/0065745 A1 | 3/2015 | McSpadden et al. | |

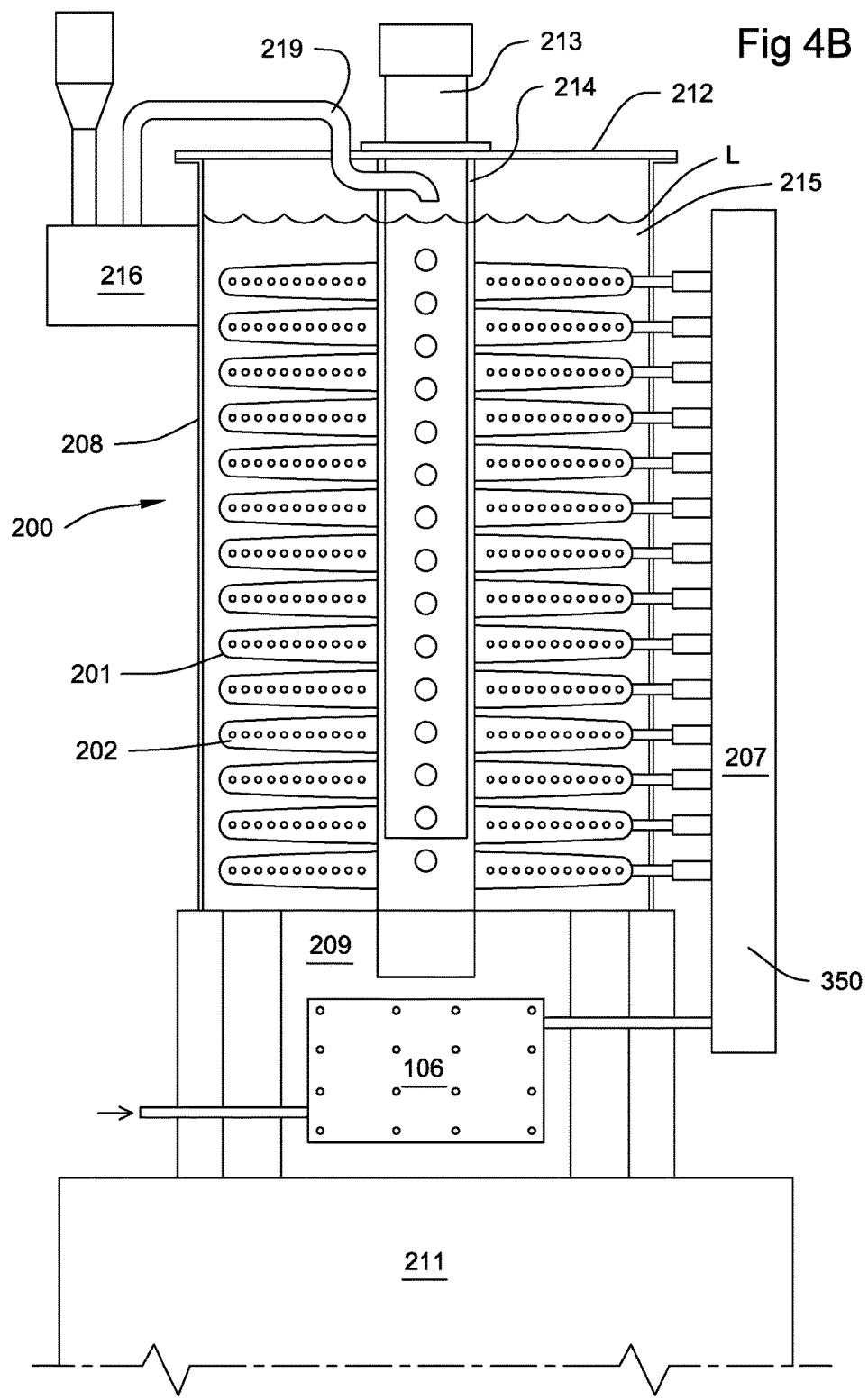

Figure 6A

| Test | Method | Limits | Results |
|---|---|---|---|
| API Gravity @ 60°F | ASTM D4052 | Report | 28.0 |
| Specific Gravity @ 60°F | ASTM D4052 | Report | 0.8871 |
| Viscosity CST @ 40°C mm$^2$/sec. | ASTM D445 | 1.9 - 6.0 | 2.10 |
| Flashpoint °C | ASTM D93 | 130 min. | 132 |
| Total Acid mgKOH/g | ASTM D664 | 0.50 max. | 0.44 |
| Sulfated Ash,% mass | ASTM D874 | 0.020 max. | 0.004 |
| Water/Sediment, %vol | ASTM D2709 | 0.050 max. | <0.010 |
| Carbon Residue,% mass | ASTM D4530 | 0.050 max. | 0.028 |
| Cloud Point, °C | ASTM D2500 | Report | 5 |
| Copper Corrosion | ASTM D130 | 3 max. | 1b |
| Cetane | ASTM D613 | 47 min. | 47 |
| Sulfur,% mass (ppm) | ASTM D5453 | 15 max. | 8 |
| Phosphorus,% mass (ppm) | ASTM D4951 | 0.001 max. | <0.001 |
| Calcium/Magnesium Combined, ppm | EN 14538 | 5 max. | <1 |
| Sodium/Potassium Combined, ppm | EN 14538 | 5 max. | <1 |
| DistillationTemp. 90% @ °C | ASTM D1160 | 360 max. | 330 |
| Oxidation Stability | EN 14112 | 3 hours min. | 190 minutes |
| Methanol,% mass (ppm) | EN 14110 | 0.2 max. | 0.0053 |
| Cold Soak Filtration | ASTM D7501 | 360 max. | 202.14 |
| Total Glycerine,% mass (ppm) | ASTM D6584 | 0.240 max. | 0.233 |
| Free Glycerine,% mass (ppm) | ASTM D6584 | 0.020 max. | <0.005 |
| Monoglycerides,% mass (ppm) | ASTM D6584 | Report | 0.047 |
| Diglycerides,% mass (ppm) | ASTM D6584 | Report | 0.006 |
| Triglycerides,% mass (ppm) | ASTM D6584 | Report | 0.001 |

Figure 6B

| Test | Method | Limits | Results |
|---|---|---|---|
| API Gravity @ 60°F | ASTM D4052 | Report | 28.93 |
| Specific Gravity @ 60°F | ASTM D4052 | Report | 0.8820 |
| Viscosity CST @ 40°C mm$^2$/sec. | ASTM D445 | 1.9 - 6.0 | 2.19 |
| Flashpoint °C | ASTM D93 | 130 min. | 133 |
| Total Acid mgKOH/g | ASTM D664 | 0.50 max. | 0.0002 |
| Sulfated Ash,% mass | ASTM D874 | 0.020 max. | 0.002 |
| Water/Sediment, %vol | ASTM D2709 | 0.050 max. | <0.010 |
| Carbon Residue,% mass | ASTM D4530 | 0.050 max. | 0.017 |
| Cloud Point, °C | ASTM D2500 | Report | 5 |
| Copper Corrosion | ASTM D130 | 3 max. | 1b |
| Cetane | ASTM D613 | 47 min. | 47 |
| Sulfur,% mass (ppm) | ASTM D5453 | 15 max. | 1.7 |
| Phosphorus,% mass (ppm) | ASTM D4951 | 0.001 max. | <0.001 |
| Calcium/Magnesium Combined, ppm | EN 14538 | 5 max. | <1 |
| Sodium/Potassium Combined, ppm | EN 14538 | 5 max. | <1 |
| DistillationTemp. 90% @ °C | ASTM D1160 | 360 max. | 330 |
| Oxidation Stability | EN 14112 | 3 hours min. | 190 minutes |
| Methanol,% mass (ppm) | EN 14110 | 0.2 max. | 0.0018 |
| Cold Soak Filtration | ASTM D7501 | 360 max. | 209.2 |
| Total Glycerine,% mass (ppm) | ASTM D6584 | 0.240 max. | 0.023 |
| Free Glycerine,% mass (ppm) | ASTM D6584 | 0.020 max. | 0.016 |
| Monoglycerides,% mass (ppm) | ASTM D6584 | Report | 0.018 |
| Diglycerides,% mass (ppm) | ASTM D6584 | Report | 0.001 |
| Triglycerides,% mass (ppm) | ASTM D6584 | Report | 0.001 |

Figure 6C

| Test | Method | Limits | Results |
|---|---|---|---|
| API Gravity @ 60°F | ASTM D4052 | Report | 29.3 |
| Specific Gravity @ 60°F | ASTM D4052 | Report | 0.8800 |
| Viscosity CST @ 40°C mm$^2$/sec. | ASTM D445 | 1.9 - 6.0 | 2.07 |
| Flashpoint °C | ASTM D93 | 130 min. | 133 |
| Total Acid mgKOH/g | ASTM D664 | 0.50 max. | 0.0017 |
| Sulfated Ash,% mass | ASTM D874 | 0.020 max. | 0.0008 |
| Water/Sediment, %vol | ASTM D2709 | 0.050 max. | <0.010 |
| Carbon Residue,% mass | ASTM D4530 | 0.050 max. | 0.009 |
| Cloud Point, °C | ASTM D2500 | Report | 5 |
| Copper Corrosion | ASTM D130 | 3 max. | 1b |
| Cetane | ASTM D613 | 47 min. | 47 |
| Sulfur,% mass (ppm) | ASTM D5453 | 15 max. | 1.6 |
| Phosphorus,% mass (ppm) | ASTM D4951 | 0.001 max. | <0.001 |
| Calcium/Magnesium Combined, ppm | EN 14538 | 5 max. | <1 |
| Sodium/Potassium Combined, ppm | EN 14538 | 5 max. | <1 |
| DistillationTemp. 90% @ °C | ASTM D1160 | 360 max. | 328 |
| Oxidation Stability | EN 14112 | 3 hours min. | 190 minutes |
| Methanol,% mass (ppm) | EN 14110 | 0.2 max. | 0.0023 |
| Cold Soak Filtration | ASTM D7501 | 360 max. | 211.48 |
| Total Glycerine,% mass (ppm) | ASTM D6584 | 0.240 max. | 0.043 |
| Free Glycerine,% mass (ppm) | ASTM D6584 | 0.020 max. | <0.002 |
| Monoglycerides,% mass (ppm) | ASTM D6584 | Report | 0.034 |
| Diglycerides,% mass (ppm) | ASTM D6584 | Report | <0.001 |
| Triglycerides,% mass (ppm) | ASTM D6584 | Report | <0.001 |

Figure 6D

| Test | Method | Limits | Results |
|---|---|---|---|
| API Gravity @ 60°F | ASTM D4052 | Report | 29.3 |
| Specific Gravity @ 60°F | ASTM D4052 | Report | 0.8800 |
| Viscosity CST @ 40°C mm$^2$/sec. | ASTM D445 | 1.9 - 6.0 | 2.10 |
| Flashpoint °C | ASTM D93 | 130 min. | 133 |
| Total Acid mgKOH/g | ASTM D664 | 0.50 max. | <0.001 |
| Sulfated Ash,% mass | ASTM D874 | 0.020 max. | <0.001 |
| Water/Sediment, %vol | ASTM D2709 | 0.050 max. | <0.010 |
| Carbon Residue,% mass | ASTM D4530 | 0.050 max. | <0.001 |
| Cloud Point, °C | ASTM D2500 | Report | 5 |
| Copper Corrosion | ASTM D130 | 3 max. | 1b |
| Cetane | ASTM D613 | 47 min. | 47 |
| Sulfur,% mass (ppm) | ASTM D5453 | 15 max. | 1.8 |
| Phosphorus,% mass (ppm) | ASTM D4951 | 0.001 max. | <0.001 |
| Calcium/Magnesium Combined, ppm | EN 14538 | 5 max. | <1 |
| Sodium/Potassium Combined, ppm | EN 14538 | 5 max. | <1 |
| DistillationTemp. 90% @ °C | ASTM D1160 | 360 max. | 331 |
| Oxidation Stability | EN 14112 | 3 hours min. | 190 minutes |
| Methanol,% mass (ppm) | EN 14110 | 0.2 max. | 0.0021 |
| Cold Soak Filtration | ASTM D7501 | 360 max. | 210.20 |
| Total Glycerine,% mass (ppm) | ASTM D6584 | 0.240 max. | 0.037 |
| Free Glycerine,% mass (ppm) | ASTM D6584 | 0.020 max. | <0.001 |
| Monoglycerides,% mass (ppm) | ASTM D6584 | Report | <0.001 |
| Diglycerides,% mass (ppm) | ASTM D6584 | Report | <0.001 |
| Triglycerides,% mass (ppm) | ASTM D6584 | Report | <0.001 |

Figure 6E

| Test | Method | Limits | Results |
|---|---|---|---|
| API Gravity @ 60°F | ASTM D4052 | Report | 29.3 |
| Specific Gravity @ 60°F | ASTM D4052 | Report | 0.8800 |
| Viscosity CST @ 40°C mm²/sec. | ASTM D445 | 1.9 - 6.0 | 2.10 |
| Flashpoint °C | ASTM D93 | 130 min. | 133 |
| Total Acid mgKOH/g | ASTM D664 | 0.50 max. | <0.001 |
| Sulfated Ash,% mass | ASTM D874 | 0.020 max. | <0.001 |
| Water/Sediment, %vol | ASTM D2709 | 0.050 max. | <0.010 |
| Carbon Residue,% mass | ASTM D4530 | 0.050 max. | <0.001 |
| Cloud Point, °C | ASTM D2500 | Report | 5 |
| Copper Corrosion | ASTM D130 | 3 max. | 1b |
| Cetane | ASTM D613 | 47 min. | 47 |
| Sulfur,% mass (ppm) | ASTM D5453 | 15 max. | 1.6 |
| Phosphorus,% mass (ppm) | ASTM D4951 | 0.001 max. | <0.001 |
| Calcium/Magnesium Combined, ppm | EN 14538 | 5 max. | <1 |
| Sodium/Potassium Combined, ppm | EN 14538 | 5 max. | <1 |
| DistillationTemp. 90% @ °C | ASTM D1160 | 360 max. | 329 |
| Oxidation Stability | EN 14112 | 3 hours min. | 190 minutes |
| Methanol,% mass (ppm) | EN 14110 | 0.2 max. | 0.00012 |
| Cold Soak Filtration | ASTM D7501 | 360 max. | 210.20 |
| Total Glycerine,% mass (ppm) | ASTM D6584 | 0.240 max. | 0.0069 |
| Free Glycerine,% mass (ppm) | ASTM D6584 | 0.020 max. | <0.001 |
| Monoglycerides,% mass (ppm) | ASTM D6584 | Report | <0.001 |
| Diglycerides,% mass (ppm) | ASTM D6584 | Report | <0.001 |
| Triglycerides,% mass (ppm) | ASTM D6584 | Report | <0.001 |

METHOD OF MANUFACTURING BIO-DIESEL AND REACTOR

PRIORITY CLAIM

This application is a continuation of U.S. application Ser. No. 14/012,810 (U.S. Pat. No. 9,475,029) filed on Aug. 28, 2013, which is hereby incorporated by reference in its entirety.

BACKGROUND OF THE INVENTION

Field of the Invention

The invention relates to the production of bio-diesel in general and high efficiency production of bio-diesel in particular.

Prior Art

The production of bio-diesel from waste oils is known. The feed stock is commonly comprised of glycerides and free fatty acids. Glycerides consist of one to three long chain fatty acids bound to a glycerol molecule. Glycerides are often present in the form of vegetable or animal oils or fats, such as those available as used cooking grease (fats, oils, and grease—FOG). The feed stock may also often contain soluble and insoluble impurities such as proteins, sugars, detergents, emulsifiers and degradation products of the FOGs generated during their use or storage.

The raw stock is usually quite viscous. In the prior art, the raw stock is commonly heated to temperatures greater than 180° F. to make the raw stock flowable and filterable. Heating the raw stock creates several problems. It is energy intensive, and thus expensive. It also results in the release of volatile organic compounds (VOCs). These either must be captured, which increases costs or they are released into the atmosphere, resulting in pollution. Heating the raw stock is also responsible for the release of nuisance odors into the atmosphere. While not necessarily a health hazard, the emission of these odors is unpleasant for workers and those who work or live proximate to a location where the raw stock is being processed.

Heating the raw stock also has adverse effects on sulfur content. Sulfur is commonly present in the raw stock at levels above 0.1 percent by volume (1000 parts per million or ppm). However, the sulfur contaminants are typically associated with the water phase of the raw stock. Heating the raw stock can cause the sulfur contaminants to disassociate from the water phase and disperse into the FOG. This can make it difficult and expensive to achieve the 0.0015 percent by volume (15 ppm) sulfur ceiling imposed by U.S. federal regulations on highway diesels and even lower sulfur ceilings in place in other countries, particularly in Europe.

Once the raw stock is fluidized and filtered, mono-alkyl esters (bio-diesel) are formed by reacting the glycerides and free fatty acids with alcohol, typically methanol or ethanol, in the presence of catalysts. A catalyst such as a strong acid (e.g. sulfuric acid) is used to facilitate the reaction of alcohol with the free fatty acids. The acid is then neutralized with a strong base such as sodium hydroxide. The stock/bio-diesel mixture is rinsed to remove the salts formed during acid neutralization. Additional strong base and additional alcohol are then added to react with the remaining glycerides to form bio-diesel and glycerol. The glycerol by-product and catalyst are separated and removed and waste water must be removed and treated as well.

OBJECTS OF THE INVENTION

It is an object of the invention to provide a reactor that can efficiently process a wide variety of feed stocks.

It is another object of the invention to produce high quality, low sulfur bio-diesel.

It is yet another object of the invention to produce bio-diesel without the use of a supplemental catalyst.

It is still another object of the invention to produce bio-diesel efficiently.

It is yet another object of the invention to produce bio-diesel quickly.

It is still another object of the invention to minimize the environmental effects of producing bio-diesel.

It is yet another object of the invention to produce bio-diesel in a continuous process.

SUMMARY OF THE INVENTION

The present invention involves the use of super-critical alcohol, preferably methanol, to react with glycerides and free fatty acids in a refined feed stock. The use of super-critical alcohol allows the reaction to proceed without a supplemental catalyst. The refined feed stock and alcohol are emulsified and forced through a reactor. The reactor is designed to utilize heat efficiently in order to minimize the energy needs of the system. Non-laminar, and preferably turbulent, flow is maintained throughout the reactor which effectively and thoroughly mixes the super-critical alcohol with the glycerides and fatty acids in the emulsion. This minimizes the amount of alcohol required to complete the reaction while simultaneously reducing the amount of time required to complete the reaction. Waters in the emulsion are maintained at elevated temperatures and pressures, typically in the sub-critical range for water. This will help solubilize the glycerides in the waters, enhancing contact between the glycerides and the alcohols. The presence of the high temperature, high pressure waters will also help break the glycerol-fatty acid bonds and inhibit dehydration of the alcohols and glycerin.

BRIEF DESCRIPTION OF THE DRAWINGS

FIG. 4B is a side cut-away view of the reactor and basin of FIG. 4A cut along line B-B.

FIG. 6A is a chart illustrating the chemical properties of the bio-diesel produced in Example 1.

FIG. 6B is a chart illustrating the chemical properties of the bio-diesel produced in Example 2.

FIG. 6C is a chart illustrating the chemical properties of the bio-diesel produced in Example 3.

FIG. 6D is a chart illustrating the chemical properties of the bio-diesel produced in Example 4.

FIG. 6E is a chart illustrating the chemical properties of the bio-diesel produced in Example 5.

DETAILED DESCRIPTION OF THE INVENTION

Figure 1A:
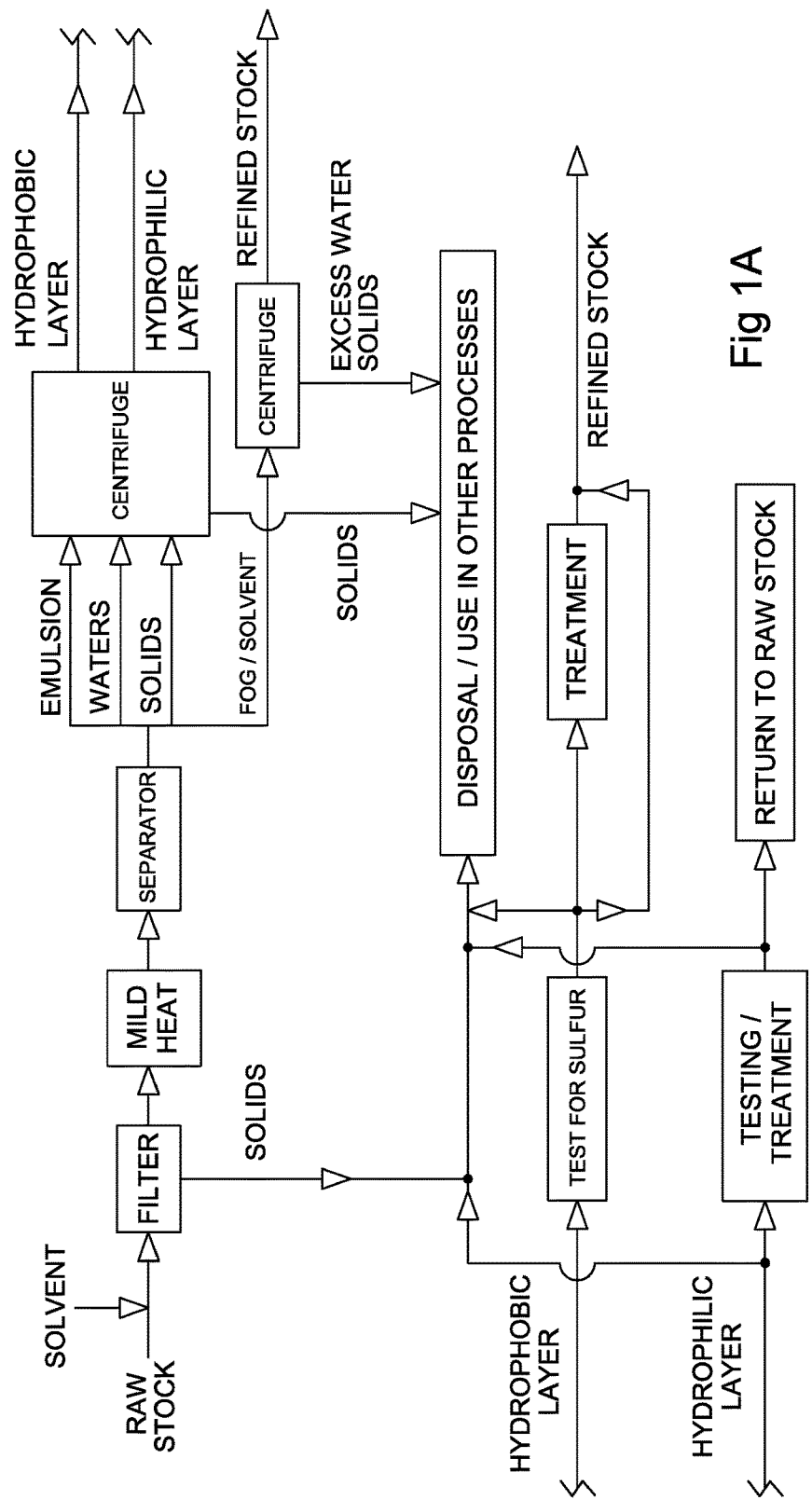
FIG. 1A is a flow chart illustrating a preferred method for preparing refined stock from raw stock.
Figure 2A:
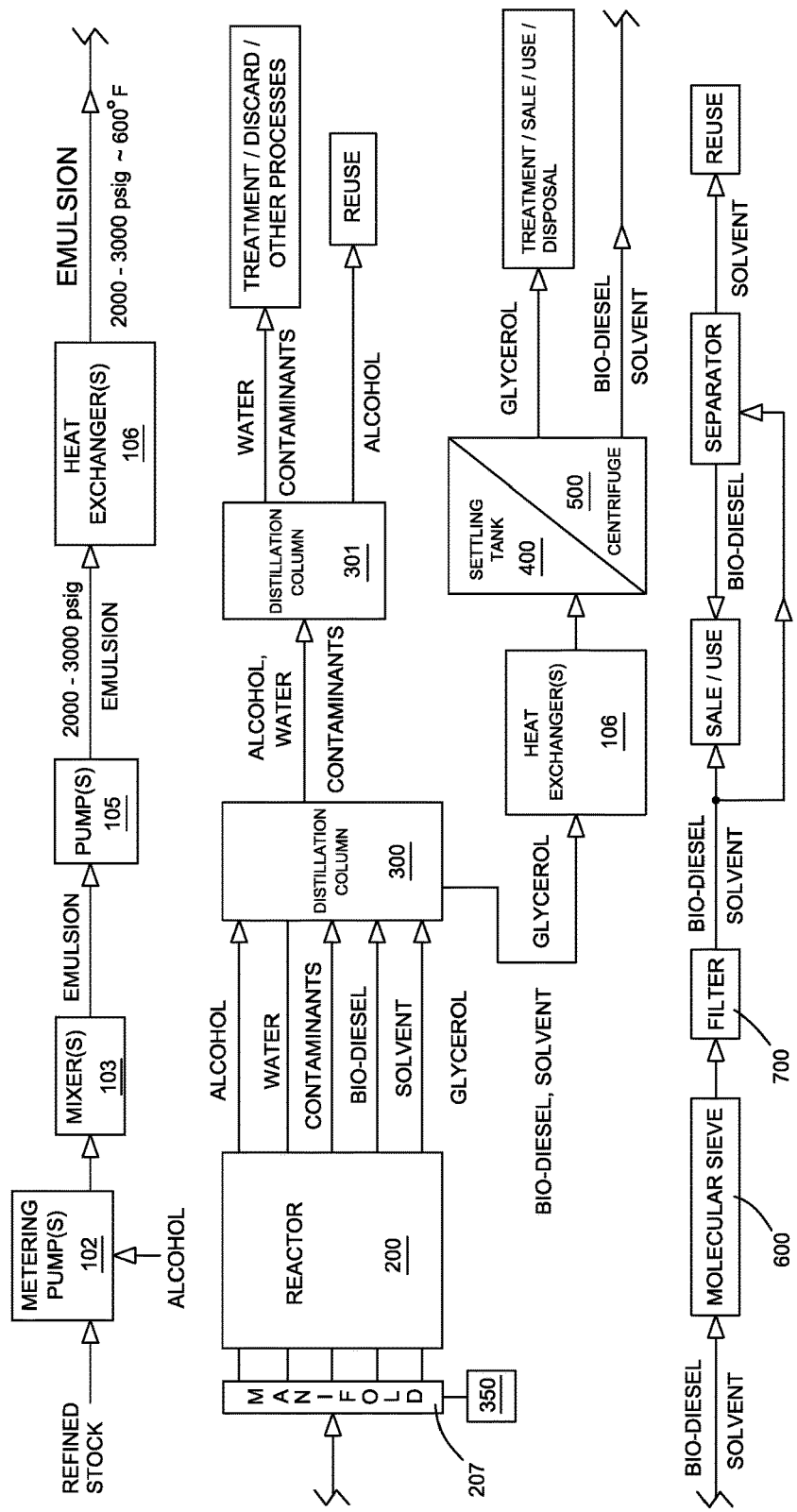
FIG. 2A is a flow chart illustrating a preferred method of forming bio-diesel from refined stock.
Figure 3A:
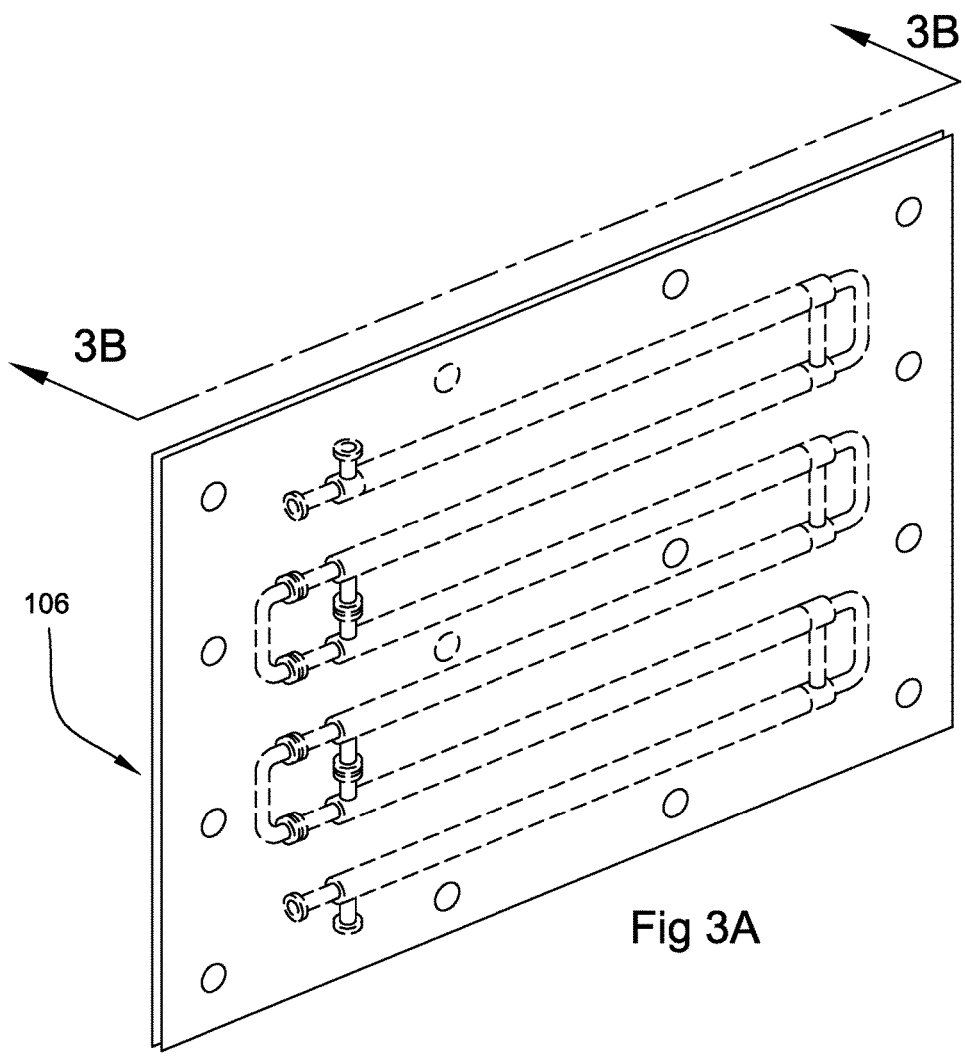
FIG. 3A is a perspective view of a preferred embodiment of a heat exchanger.
Figure 3B:
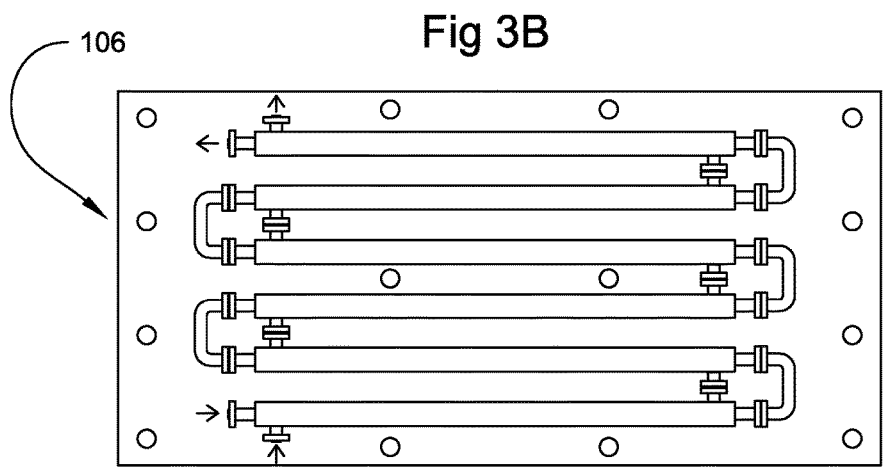
FIG. 3B is a cross-section of the heat exchanger illustrated in FIG. 3A.
Figure 4A:
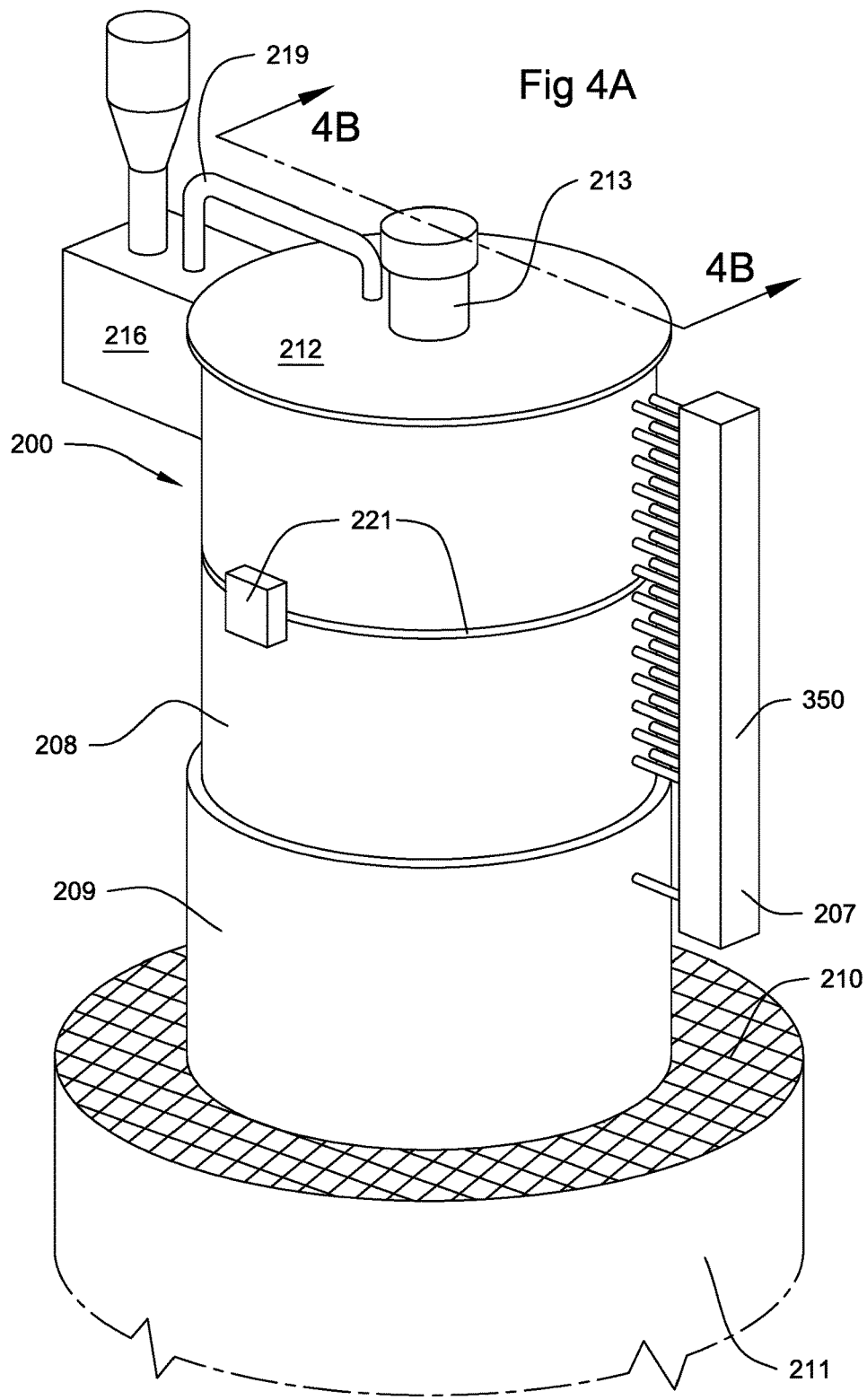
FIG. 4A is a perspective view of a preferred embodiment of a reactor and overflow basin.
Figure 5A:
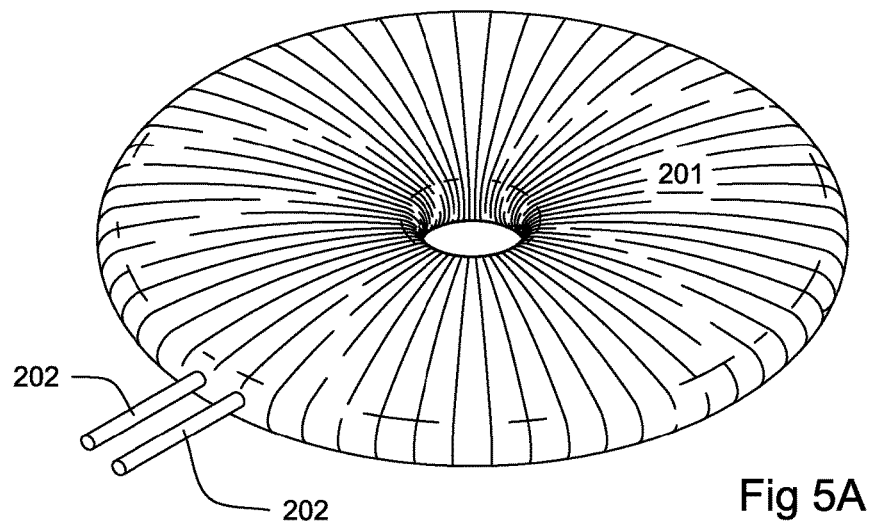
FIG. 5A is a perspective view of a preferred embodiment of a shell.
Figure 5B:
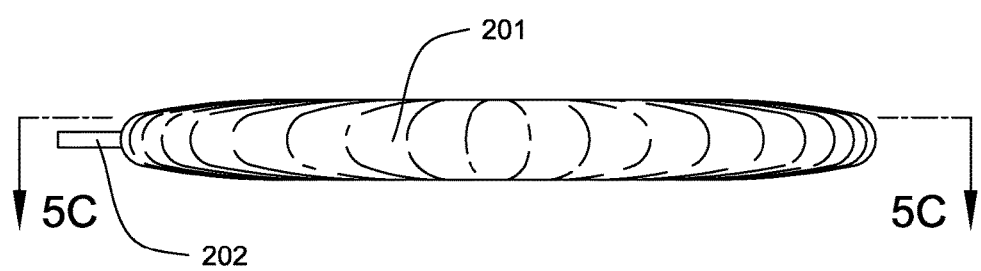
FIG. 5B is an end view of a preferred embodiment of a shell.
Figure 5C:
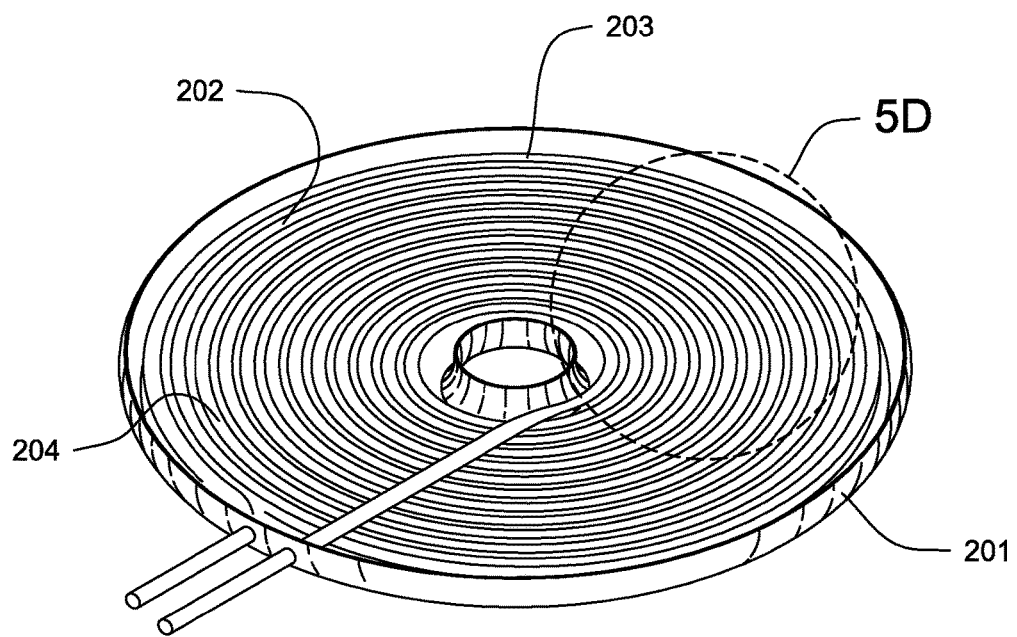
FIG. 5C is a cut-away perspective view of a preferred embodiment of a shell, illustrating the reaction line coil within.
Figure 5D:
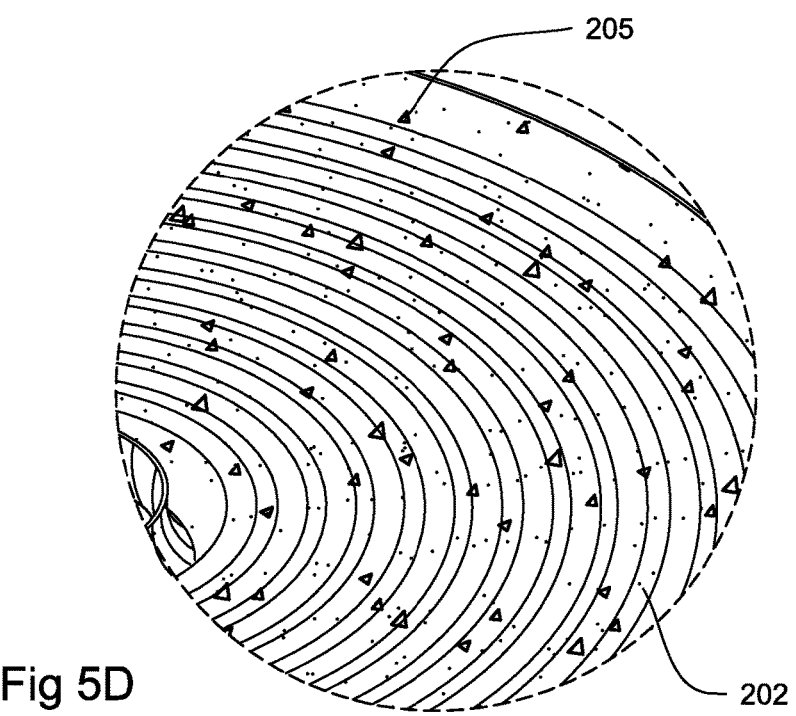
FIG. 5D is a detail view of a portion of 5C identified therein, with the packing material shown in reduced quantities for illustration purposes.

The raw stock may be any source of glycerides and/or free fatty acids. Potential sources of raw stock include used cooking oils; the fat, oil, and grease ("FOG") from a grease interceptor or trap; and the "float" from a sewage treatment tank or lagoon—i.e., the high fat content layer typically found floating in early stage sewage treatment. The raw stock will typically contain from about ten to eighty percent water, by volume; about fifteen to fifty percent solid waste, by volume; and from about 2.5 to about fifty percent FOG by volume. As noted above, the raw stock is typically quite viscous. Although the properties of typical raw stocks are provided above, it should be noted that one of the advantages of the present invention is its ability to work with a wide range of raw stocks.

In practice, the raw stock typically arrives by truck. The raw stock is first treated by passing it through a filter, preferably of about 2300 microns, in order to remove the larger solids. In the preferred embodiment, an hydrophobic solvent is added to make the raw stock sufficiently flowable and filterable. Quantities of solvent may be up to fifty percent by volume of the FOG phase of the raw stock. While it is desirable to limit the amount of solvent utilized, a sufficient amount should be used to keep the raw stock flowing through the filter. Typically about twenty percent by volume of the FOG phase of the raw feed stock will be sufficient to achieve the necessary fluidity.

The raw stock and solvent may be heated, but to temperatures less than about 120° F., and preferably to about 110° F. This avoids many of the problems created by heating the stock to make it flowable. In systems where the stock is heated to achieve fluidity, venting or vapor controls are usually required. Because most noxious components are not volatized at the lower temperatures of the preferred embodiment, no such systems are necessary.

Many appropriate solvents will dissolve the waste FOGs. Diesel oil is a suitable solvent, particularly when the end product is expected to be used in a diesel/bio-diesel blend. Bio-diesel is a preferred solvent as any carry-over can be included in the product regardless of the intended use of the end product. When the solvent needs to be separated from the end product, use of a solvent with a lower gel point than bio-diesel will usually be preferred, as the relatively high gel point of bio-diesel is a convenient way to effect separation.

Once fluidized the raw stock and solvent are moved to a separation vessel where they are allowed to settle, preferably for up to twenty-four hours. This will result in the formation of four distinct layers: a layer of solids less than 2300 microns on the bottom; a clear water phase commingled with the solids and typically extending above it, depending upon volume; an emulsion phase located above the water phase; and an FOG/solvent phase at the upper layer.

The upper FOG/solvent layer is pumped off and stored. If desired to facilitate pumping or any other reason, the height of the upper FOG/solvent layer may by raised by adding water.

The remaining layers are passed through a 1200 micron filter to remove the majority of the remaining manmade solids. The filtrate is preferably then centrifuged. In the preferred embodiment, the filtrate is first passed through a decanter centrifuge to remove the majority of solids greater than twenty microns in diameter and then through a disc stack centrifuge to remove the majority of solids greater than five microns in diameter. The disc stack centrifuge will also separate the emulsion layer into an hydrophobic layer and a hydrophillic and water layer. The hydrophobic layer will be less than ten percent water by volume.

The hydrophillic components and waters are separated and treated for reintroduction into the process, use in other processes, as appropriate or eventual discharge into a municipal sewage system or other suitable receiving body.

The hydrophobic layer is tested for sulfur content. If the sulfur content of the hydrophobic layer exceeds 1000 ppm remediation is in order. Depending upon the chemistry of the hydrophobic layer, it may be treated with an acid solution having a pH of about 3.0 or below or a basic solution with a pH of about 13.0 or above to separate contaminant functional groups from fatty acid backbones. After separation, the fatty acid backbones may be returned to the feed stock for processing into bio-diesel; or the hydrophobic layer may be diverted for use in another process. However, it will be noted that the hydrophobic layer typically comprises only about one to two percent by volume of the raw feed stock. Many of the sulfur contaminants are often present in this layer. Accordingly, it often makes sense to discard this layer or to divert it for use in another process rather than attempting to remediate and process into bio-diesel the FOG and glycerides it may contain.

The upper FOG/solvent layer is passed through the same filtration and centrifuge steps discussed above in order to remove solids above five microns and to reduce the water content below about ten percent by volume.

The raw stock/solvent may be warmed slightly to enhance flowability. However, in all of the foregoing filtration and centrifuge steps, the temperature is preferably maintained below about 120° F. and preferably at about 110° F. It will be appreciated that many of the water soluble sulfur contaminants present in the raw stock will be removed with the waters as the lower temperatures of the preferred process will result in fewer of the sulfur contaminants becoming disassociated from the waters.

The filtered and centrifuged FOG/solvent layer will be combined with the hydrophobic component that was separated from the emulsion layer, assuming that either the hydrophobic component did not contain excessive amounts of sulfur or that it was treated. At this stage, the mixture should preferably be about 2.5 percent or less solids, by volume, with the solids having a diameter of about 5 microns or smaller. Water should comprise about ten percent by volume or less. More than about eighty-five percent by volume, and preferably more than about eighty-seven percent by volume should be glycerides, free fatty acids, and solvent. In addition, there will be relatively small amounts (less than about 0.05 percent and most preferably less than about 0.01 percent, by volume (less than about 500 ppm and most preferably less than about 100 ppm)) of other lipids (e.g., sphingolipids, glycolipids, and phospholipids); detergents (e.g., long chain fatty alcohols, alcohol ethoxylates and alcohol ethoxysulfates (AES) and organosulfates); and surfactants. Stock meeting these criteria is referred to as refined feed stock. It should be understood that refined feed stock may be obtained from a raw stock in the manner described above or it may be obtained in a form that already satisfies these conditions. Examples of stock that qualifies as refined feed stock would include used cooking oils and unrefined fats, oils and greases of animal or plant origin filtered to remove solids greater than 5 microns in size.

The refined feed stock is next mixed with alcohol, preferably methanol, though other alcohols may be used. Suitable alcohols will have a critical point below 650° F. and 2500 psig. Linear and branched alcohols having chains of up to five carbons are expected to be suitable. Examples include ethanol, propanol, butanol, and pentanol. The appropriate molar ratio ranges from about 3:1 to 15:1 alcohol to glycerides in the refined feed stock, and preferably about 9:1 to 12:1. In practice, the alcohol levels will simply be reduced as low as possible while still obtaining, preferably in one pass, substantially complete conversion of the glycerides and free fatty acids to mono-alkyl esters. This may be verified by using gas chromatography to analyze the refined feed stock and the finished product. Gas chromatography or other suitable analytic methods will provide the molar content of the glycerides and free fatty acids in the feed stock and confirm that substantially all of the glycerides and free fatty acids have been converted to mono-alkyl esters. Examples are provided below.

It will be appreciated that the highest alcohol demands will be encountered in refined feed stocks having the highest triglyceride content. Vegetable oils are an example of such a refined feed stock. Triglycerides require more alcohol on a molar basis because each of the three fatty acid chains must be reacted with a separate alcohol molecule in order to achieve complete esterification. That is, one mole of triglyceride will release three moles of fatty acid, each of which must be reacted with a mole of alcohol. Refined feeds stocks that comprise a greater percentage of mono- and di-glycerides will require proportionally less alcohol to complete esterification. In view of the foregoing, it will be appreciated that the molar ratio necessary to completely esterify a refined feed stock whose fatty acids are substantially all in the form of triglycerides represents the maximum amount of alcohol expected to be required. The inventors have determined that a 15:1 molar ratio of alcohol to glyceride is sufficient to substantially complete esterification of a refined feed stock whose glycerides are substantially all in the form of triglycerides, e.g., refined and deodorized vegetable oils and animal fats. Lower molar ratios will be suitable for refined feed stocks whose glyceride content is more varied.

When there are substantially no glycerides present in the refined feed stock, that is when the fatty acids are present as free fatty acids, obviously it does not make sense to speak of a ratio of moles of alcohol to moles of glyceride. Here the relevant ratio is moles of alcohol to moles of fatty acid. In this context, only one mole of alcohol will be needed to react with each mole of free fatty acid. Although some excess alcohol is required to ensure that the reaction proceeds expeditiously, molar ratios of as low as 3:1 (alcohol to fatty acid) are suitable.

Regardless of the source of the fatty acids—whether they are present in and must be freed from a glyceride molecule or if they are present as free fatty acids in vegetable oil or the like—the alcohol requirements by weight are relatively small. To achieve the necessary molar ratios, alcohol in the amount of about seven to about twenty-one percent by weight of the emulsion exiting the mixer will be adequate for most refined stocks. In the majority of cases, alcohol between about twelve and about sixteen percent by weight of the emulsion will suffice.

The alcohol and refined feed stock are preferably mixed using metering pumps 102, most preferably one for the alcohol and one for the refined feed stock. This allows the target amount of alcohol to be used, thereby ensuring that sufficient alcohol is present for both the desired reaction and the formation of the desired emulsion while avoiding the unnecessary addition of excess alcohol. Suitable metering pumps include positive displacement diaphragm pumps such as those available from DXP Enterprises of New Orleans, La.

The mass of the feed stock will vary depending upon the amount of water present, the amount of glycerides present, and the amount of solvent present as well as the nature of the solvent. A refined feed stock comprised of about fourteen to about twenty-seven percent solvent by weight of the emulsion exiting the mixer is preferred, and most preferably about twenty to about twenty-two percent solvent by weight. Typical density of the preferred feed stock can be expected to be about 500 gm/ml. Densities above about 600 gm/ml, particularly when the water content of the feed stock is low (below about two percent by volume), is indicative of higher amounts of triglycerides and/or diglycerides and suggests a need for greater amounts of alcohol.

A water-in-oil meter is preferably used to determine the amount of water present in the feed stock. Suitable meters include the in-line meters available from EESiFlo North America of Mechanicsburg, Pa. A mass flow meter is preferably used to determine the mass of the feed stock. Suitable meters include the in-line mass flow meters available from Yokogawa of North America of Houston, Tex. The output of these meters is used to adjust metering pumps 102 for the alcohol and/or the refined feed stock to obtain the desired molar ratio.

After the desired feed stock and alcohol ratios are established, the alcohol and feed stock mixture is preferably passed through one or more mixers 103, preferably an in-line high shear mixer. Suitable high shear mixers include the Greerco Inline Pipe High Shear Mixer available from Chemineer, a division of Robbins & Meyers, Inc. of Willis, Tex. The alcohol and feed stock should exit the high shear mixer as a stable emulsion with an average droplet diameter on the order of $1\times10^{-7}$ to $10^{-8}$ m.

The emulsion is preferably passed through a mass flow meter to confirm the emulsion's stability. Suitable mass flow meters include the Coriolis in-line mass flow meter available from Yokogawa of North America, headquartered in Houston, Tex. The mass flow meter will ideally indicate a density of about 1.0 kg/l±0.5 kg/l.

The emulsion will typically be at or near ambient temperature and pressure. It is next heated and pressurized. Either step may occur first; however, in the preferred embodiment the emulsion is pressurized first. In the preferred embodiment, the emulsion is passed through one or more pumps 105, preferably a high pressure piston pump, such as the Hydra Cell pump available from Wanner Engineering, Inc. of Minneapolis, Minn. The pressurized emulsion should preferably be between about 2000 and 3000 pounds per square inch gauge (psig), and most preferably about 2500 psig.

The emulsion is passed through one or more heat exchangers 106. Heat exchangers 106 are preferably shell and tube exchangers, preferably embodying a single pass shell, counter-current flow design. Materials and construction techniques for heat exchangers 106 should be selected so that heat exchangers 106 will be substantially chemically inert to the emulsion under the desired heat transfer conditions and so that heat exchangers 106 can withstand the anticipated temperatures and pressures to which heat exchangers 106 will be subject. Although shell and tube designs are expected to be sufficient to achieve the thermal objectives in the preferred application, other heat exchanger designs, such as spiral or plate heat exchangers may be utilized according to the heat transfer need specific to the application. Additionally, heat exchangers 106 may be provided with fins or other obstructive elements to enhance heat transfer between the two flows. Heat exchangers suitable for use in the preferred embodiment may be obtained from Tranter, Inc. of Wichita, Falls, Tex.

Exiting heat exchanger 106, the emulsion should preferably be between about 550° to 620° F. and most preferably at about 600° F. The pressure will be relatively unchanged.

In one preferred embodiment, multiple heat exchangers 106 are provided. One or more are provided outside of reactor 200 (discussed below) and at least one heat exchanger 106 is positioned inside reactor 200, or more preferably inside reactor reservoir 209. In this embodiment, the emulsion exits the heat exchangers 106 external to reactor 200 between about 440° and 460° F. and most preferably at about 450° F. The pressurized emulsion is then passed through the heat exchanger 106 positioned inside reactor reservoir 209. The emulsion will exit the internal heat exchanger 106 between about 550° and 620° F. and most preferably at about 600° F. The pressure will be relatively unchanged. By utilizing the heat exchanger 106 contained in reservoir 209, the emulsion may be efficiently brought to the desired reaction temperature immediately prior to entering reactor 200.

It will be appreciated that at these temperatures and pressures, the alcohol will be super-critical (i.e., above the critical point), the water will be sub-critical (i.e., above the atmospheric boiling point but below the critical pressure and temperature of 3210 psig and 705° F.). However, the entire emulsion is believed to behave as a homogenous, super-critical fluid, as discussed in more detail below.

The now pressurized and heated emulsion will enter the reactor 200. Reactor 200 is comprised of one or more shells 201, preferably tubular in shape and most preferably configured in the approximate shape of a ring torus. Shells 201 are preferably constructed from thermo-conductive materials such as silicon carbide, carbon steel or other steel alloys. The material for shell 201 should be substantially chemically and physically inert to heat transfer media 215 under the expected operating conditions of reactor 200 and it should be physically strong enough to sustain and direct the burst pressure from reaction line 20 (discussed below) in the event of a reaction line failure. In the preferred embodiment, shell 201 is comprised of ABS A-grade carbon steel with a wall thickness of about 0.25 inches.

Inside each shell 201 is a reaction line 202 through which the pressurized and heated emulsion travels. Reaction lines 202 are preferably configured in the shape of a coil 203. Reaction lines 202 should resist corrosion by the materials contained within them and should be physically strong enough to withstand the pressure the emulsion is under. A three to one safety ratio is preferred, meaning that reaction lines 202 should be comprised of materials of sufficient thickness and strength to withstand three times the amount of force to which reaction lines 202 are expected to be exposed. The particular composition of reaction line 202 will depend upon the nature of the emulsion and the conditions at which reactor 200 is operated. In a preferred embodiment, reaction line 202 is comprised of 316 stainless steel tubing having an outside diameter of about one half inch, a wall thickness of about 0.065 inches, and an inside diameter of about 0.37 inches.

In sizing reaction line 202, several objectives should be kept in mind. The pressure to which the emulsion will be subjected will effect the minimum thickness of reaction line 202. The walls of reaction line 202 must be strong enough to withstand the pressure applied to the emulsion traveling through line 202. All other things being equal, that means that greater pressures require thicker walls. Stated differently, at constant pressure a pipe with a smaller inside diameter requires thinner walls than a pipe with a greater inside diameter. Thus, increasing the inside diameter requires the walls of reaction line 202 to increase in thickness, if reaction line 202 is to withstand the pressures common within the preferred embodiment of reactor 200. All other things being equal, pipe with thinner walls will generally be less expensive and will transfer heat more readily than pipe with thicker walls.

There are costs to using smaller, thinner pipe, though. The smaller inside diameter pipe will carry less fluid at any one time than the same length of pipe with a larger inside diameter. As a result, at constant pressure, the fluid in the smaller inside diameter pipe will move faster than the fluid in the larger inside diameter pipe. If retention time is an issue and pressure is kept constant, greater lengths of small inside diameter pipe must be used to achieve the same retention time as shorter lengths of large inside diameter pipe. Thus, if pressure must be kept constant and the pipe contents must be maintained in the reactor for a requisite amount of time, a greater length of small inside diameter reaction line 202 will be required than if larger inside diameter pipe is used for reaction line 202.

In the preferred embodiment, each reaction line 202 comprises a coil 203 that includes multiple turns 204 running within and preferably along the bottom of torus shaped shell 201. In one preferred embodiment, a coil 203 comprises thirty-eight turns 204 about a radius ranging from eighteen to fifty-eight inches and has a length of 350 feet. Although in the preferred embodiment, each shell 201 includes only one reaction line 202, multiple reaction lines 202 could be included within a shell 201.

The space between shell 201 and reaction line 202 is preferably filled with chemically inert packing material 205. The optimal thermal conductivity of packing material 205 will depend upon the thermal conductivity of heat transfer media 215 (discussed below) and of shell 201. Packing material 205 should preferably have a lesser thermal conductivity than that of heat transfer media 215 and a greater thermal conductivity than shell 201. This will facilitate heat transfer across shell 201. In the preferred embodiment, packing material 205 will have a thermal conductivity at least about 200 BTU/ft·h·F.

Packing material 205 also acts as a dampener to suppress the hammer effect on reaction line 202 caused by pump 105 moving the emulsion through reaction line 202. In the preferred embodiment, the packing material is silicon carbide. Other suitable packing materials include sand or glass, depending upon intended reaction conditions. In order to prevent clogging of the safety valves or burst disks in shell 201, it is preferable that the packing material have a particle size of less than 200 microns. In the preferred embodiment, packing material 205 is 120 grit/125 micron in size with a density of 89 lbs/ft$^3$ (1.43 g/cc). The packing material 205 is typically heated in situ to remove moisture. A vacuum is then applied to ensure tight packing, maximizing contact within packing material 205 which aides in thermal conductivity.

Multiple shells 201 may be provided by stacking them within reactor 200. A framework is provided to support each shell 201 within reactor 200. The framework should position shells 201 so that they are separated from each other, preferably by at least about three inches. In the preferred embodiment, the framework will also serve as cross braces for tank 208. Preferably, the framework should be made of the same material as tank 208.

When multiple reaction lines 202 are present, they are fluidly connected. In the preferred embodiment, the pressurized emulsion flows into one end of reaction line 202, preferably passing through the wall of shell 201 and out the opposite end of reaction line 202, again preferably passing through the wall of shell 201. In the preferred embodiment, the outflow from reaction line 202 is connected to a manifold 207 comprising a plurality of valves. Manifold 207 may be configured to direct the outflow of one reaction line 202 into the inflow of the next reaction line 202 so that the emulsion may be passed through multiple shells 201 and reaction lines 202 in succession. Alternatively, the manifold 207 may direct the outflow of any reaction line 202 out of reactor 200, whereby the outflow will become the effluent from reactor 200. Manifold 207 is preferably positioned exterior to tank 208 (discussed below). Manifold 207 should preferably be provided with a plurality of sensors configured to continuously measure pressure, temperature and mass flow as the fluid enters and exits each reaction line 202 and/or shell 201. Suitable sensors are available from Thermal Solutions of Houston, Tex. The data gathered by the sensors is transmitted to a computerized control system so that the operator and/or a computerized operations program may monitor the operation of reactor 200.

The number of reaction lines 202 through which the emulsion passes may be selected by the operator and will depend upon the desired holding time for the emulsion within reactor 200. However, the longer reaction line 202, the greater the drop in pressure across line 202. Both the friction between the inner wall of reaction line 202 and the continuous angular velocity imparted to the emulsion by the curvature of coils 203 will result in loss of pressure in lines 202. Although some pressure loss is unavoidable, sufficient pressure must be maintained to keep the alcohol in the emulsion in a super-critical state. Likewise, water in the emulsion should not be allowed to boil.

One step that can be taken to minimize pressure losses in reactor 200 is to enlarge the inside diameter of lines 202; however, that has costs, as discussed above. Another step that can be taken is to enlarge in the inside diameter of the connecting lines between reaction lines 202. This will reduce the additional pressure losses that occur in reactor 200 external to lines 202. If the inside diameter of the connecting lines is increased, the connecting lines should preferably have an internal diameter that is greater than the internal diameter of reaction lines 202 by at least about twenty-five percent, but not more than about seventy-five percent.

Shell(s) 201 are contained within tank 208. Tank 208 is preferably made of carbon steel and is generally cylindrical with a thickness of about three quarters of an inch. Tank 208 is preferably open ended and rests on and within a reservoir 209, also preferably made of steel. In the preferred embodiment, a heat exchanger 106 is provided in reservoir 209.

In the preferred embodiment, reservoir 209 sits upon a grated platform 210 covering an overflow basin 211. Basin 211 should preferably be of sufficient size to contain the entire volume of tank 208 and reservoir 209. It will be appreciated that in the event of a failure of tank 208, reservoir 209, or any of the other components of reactor 200, the contents of the same may be directed to and captured in basin 211. Reservoir 209 is also preferably provided with a valve that will allow the contents of tank 208 to be discharged into basin 211.

The top of tank 208 is provided with a fluid tight lid 212. Lid 212 is also preferably made of steel and is bolted to the top of tank 208. In the preferred embodiment, a high temperature, chemically inert, metallic gasket, preferably made of hydrous aluminum silicate available from Deacon Industries of Washington, Pa., is provided between tank 208 and lid 212 to ensure a seal between lid 212 and tank 208. Chemically inert, heat compatible metallic gaskets constructed from steel and/or steel alloys may also be used.

One or more heaters 213 are positioned within tank 208. Heater 213 is preferably an electric flange heater such as those available from Thermal Solutions of Houston, Tex. Heater 213 is preferably provided with separate circuitry which may be powered independently. This will allow heater 213 to be operated from about ten percent capacity to one hundred percent capacity, avoiding the "all on/all off" pulsing common in conventional heaters.

In the preferred embodiment, heater 213 is contained within a perforated pipe 214. Pipe 214 is preferably made of the same material as tank 208. In the preferred embodiment, pipe 214 and heater 213 are vertically oriented within tank 208. When shells 201 are torus shaped, pipe 214 and heater 213 will preferably be positioned within shells 201 in alignment with the axis of the torus. It will be appreciated that in this configuration, shells 201 surround pipe 214 and heater 213 and may be positioned so that all portions of each shell 201 are roughly equidistant from heater 213.

Tank 208 is partially filled with a heat transfer media 215. Heat transfer media 215 should be selected to effectively transfer heat throughout tank 208. As discussed above, heat transfer media 215 should have thermal conductivity that is greater than that of packing material 205 and most of the other components of reactor 200 separating heat transfer media 215 from the contents of reaction line 202.

Heat transfer media 215 will heat packing material 205 across shell 201. As discussed below, heat transfer media 215 is preferably liquid while packing material is 205 preferably solid and shell 201 is also solid. Thus, convection will be the main heat transfer mechanism from heat transfer media 215 to the outer surface of shell 201. Conduction will be the predominant heat transfer mechanism from the outer surface of shell 201, through packing material 205, to the outer surface of reaction line 202.

The higher the thermal conductivity of a material, the better it will transfer heat to a cooler material. To efficiently transfer heat through reactor 200, heat transfer media 215 should have a thermal conductivity that is greater than that of shell 201 and packing material 205. Similarly, the thermal conductivity of packing material 205 should be greater than that of shell 201 and reaction lines 202. This will help prevent shell 201 from acting as a heat barrier. Rather, heat will flow from heat transfer media 215, across shell 201, through packing material 205 to reaction line 202.

In the preferred embodiment, heat transfer media 215 should preferably have a thermal conductivity value of between about 800 and about 2900 BTU/$ft^2 \cdot h \cdot F$. This can be compared to the preferred thermal conductivity of shell 201, which has a thermal conductivity of about 20 BTU/$ft^2 \cdot h \cdot F$, packing material 205 which has a thermal conductivity of about 200 BTU/$ft^2 \cdot h \cdot F$ and the thermal conductivity of the preferred material for reaction lines 202, about 20 BTU/$ft^2 \cdot h \cdot F$.

The preferred heat transfer media 215 includes a molten eutectic mixture of water soluble, inorganic salts of potassium nitrate, sodium nitrite and sodium nitrate available from Coastal Chemical Company of Abbeville, La., under the brand name Hitec. In operation, when the heat transfer media is molten salt, it will preferably be maintained between about 650° and 775° F. and most preferably at about 750° F.

Heat transfer media 215 should be filled to a level (L) above the highest shell 201, so that all shells 201 are immersed in heat transfer media 215. In the preferred embodiment, heat transfer media 215 extends from level L to the bottom of tank 208 and into reservoir 209. Level L and heater 213 are preferably positioned relative to each other so that the entire active portion of heater 213 is positioned within heat transfer media 215 and the inactive portions are positioned above level L.

One or more circulation pumps 216 are provided to circulate transfer media 215. Circulation pump 216 is preferably positioned adjacent to tank 208. Pump 216 should have an inflow line positioned below level L, and preferably at least about fifteen percent of the height of L below level L, to ensure that pump 216 is able to maintain suction with heat transfer media 215. Pump 216 should have a discharge line 219 configured to discharge into pipe 214 so that the re-circulated transfer media 215 flows directly over the coils of heater 213. Suitable circulation pumps 216 include a molten metal vertical pump such as those available from Gusher Pumps of Williamstown, Ky. (USA).

A secondary fill line may be provided. The secondary fill line would pass through tank 208 and open into pipe 214. Heat transfer media 215 may be provided through the secondary fill line, particularly at start-up. This will de-gas the area surrounding the coils of heater 213 by filling it with liquid, thereby protecting the coils and more effectively transferring heat from heater 213 to the surrounding media 215, which may be solid at start up.

In addition or in the alternative, a circulation manifold may be provided to direct the effluent of pump(s) 216 proximate to particular shells 201, as desired.

Tank 208 may also be provided with one or more external heaters 221. In the preferred embodiment, external heaters 221 are band heaters positioned on the outside of tank 208. Suitable band heaters include those available from Thermal Solutions of Houston, Tex. External heaters 221 are particularly useful during startup, when heat transfer media 215 may be solid. External heaters may be used to liquefy heat transfer media 215 from the outer edge of tank 208. It will be appreciated that if transfer media 215 has been allowed to solidify, air is likely to be trapped within transfer media 215. Heating heat transfer media 215 from the outer edge will cause the portions of transfer media 215 nearest the walls of tank 208 to liquefy first, thereby creating a vertical passage adjacent the walls of tank 208. This will tend to de-gas heat transfer media 215.

Tank 208 and reservoir 209 are preferably enclosed in insulation, such as four inch calcium silicate available from Industrial Alliance Services of Houma, La.

It will be appreciated that reservoir 209 will contain excess heat transfer media 215 which will serve as a heat battery. Once the full volume of heat transfer media 215 is heated to the desired temperature range, having a larger volume of media 215 available will prevent the overall temperature of media 215 from falling as much as a result of the heating of the emulsion. This will allow heater 213 and/or external heaters 221 to be used less often and/or at lower power levels than would otherwise be required. Reservoir 209 has a volume that is preferably at least about twenty-five percent the volume of tank 208 and may be larger depending upon the desired flow rate of the emulsion.

Heat transfer media 215 and reaction lines 202 are in thermal communication. In the preferred embodiment, heat transfer media 215 and packing material 205 ensure that thermal energy is efficiently delivered to reaction lines 202. This will facilitate the reaction between the alcohol and the fatty acids and glycerides in the emulsion, ultimately allowing esterification and transesterification to proceed more rapidly and with less alcohol per mole of glyceride.

Reactor 200 is preferably provided with several safety components. A burst disk is preferably provided in the upper end of tank 208, in or proximate to lid 212. The burst disk is fluidly connected to a discharge line configured to discharge into basin 211. Should pressure in tank 208 exceed the desired safety margin, the burst disk will allow the contents of tank 208 to flow into basin 211.

Manifold 207 is preferably provided with an isolation valve for each shell 201. In the event that a pressure increase is detected in any reaction line 202, which could indicate a blockage, or a sharp pressure drop, which could indicate a rupture, fluid flow through all reaction lines 202 in a shell 201 may be stopped and rerouted to the next reaction line 202 in an adjacent shell 201. Each reaction line 202 is preferably provided with a burst disk or safety valve fluidly connected to a discharge line. The discharge line is configured to discharge into basin 211. In the event that the isolation valve for any reaction line 202 is closed, the safety valve or burst disk should be opened, either automatically or manually, whereby the contents of the isolated reaction line may be emptied into basin 211.

Each shell 201 is preferably fitted with a burst disk. Each burst disk is fluidly connected to a discharge line configured to discharge into basin 211. Should pressure in shell 201 exceed the desired safety levels, the burst disk will allow the contents of shell 201 to flow into basin 211.

The various burst disks are preferably configured to open at pressures about twenty-five percent above the anticipated operational pressure of their respective vessels. In the preferred embodiment, all vessels (e.g., tank 208, reaction lines 202, shells 201, etc.) should be constructed to withstand pressures at least three times the anticipated burst pressures of their respective burst disks.

It will be appreciated that shells 201 are essentially safety devices. Reaction lines 202 could be immersed directly in heat transfer media 215 and the emulsion would be heated to/maintained at the desired temperature more readily than if heat is forced to flow across shell 201 and packing material 205. However, the emulsion is under very high pressure and its contents are flammable. Additionally, the preferred heat transfer media 215 is a strong oxidizer. If reaction lines 202 were in direct contact with heat transfer media 215, the risk of failure of reaction lines 202 would increase while the potential consequence of such a failure—the emulsion being ejected under very high pressure directly into molten salts— would be enhanced. By positioning reaction lines 202 within shell 201, heat transfer to the emulsion is made somewhat more difficult, but the risk of a failure of lines 202 is reduced and the potential consequences of such a failure are minimized insofar as shell 201 may temporarily contain any leak while reactor 200 is shut down and/or flow is diverted to another shell 201/reaction line 202 via manifold 207. It is also for safety reasons that the preferred design of shell 201 has a shape that approximates a torus. With few or no crevices or corners, shell 201 is better able to distribute and, thus, withstand any pressure spikes that may occur in the event of a failure of reaction line 202.

In operation, pump or pumps 105 drive the emulsion through reaction lines 202 of reactor 200. The preferred flow rate is maintained at or above 18 l/min. This flow rate is sufficient to ensure a steady flow rate throughout reaction lines 202. The continuous circular motion of the emulsion through coil shaped reaction lines 202 and the pulsing force from pumps 105 will ensure that the flow through lines 202 remains at least non-laminar, and preferably turbulent, which will ensure continuous mixing of the alcohols with the fatty acids and glycerides in the emulsion.

As noted above, the alcohols in the emulsion will be super-critical. Super-critical alcohols are known to effectively convert glycerides (including triglycerides) and free fatty acids to esters rapidly and without the need for a catalyst. It is believed that the hydrogen bond energy is lowered under super-critical conditions, effectively allowing the alcohol to behave like a free monomer. It is believed that under these conditions the alcohol molecule can directly attack the carbonyl carbon of the triglyceride.

Keeping the alcohol at super-critical conditions will also significantly enhance the ability of the alcohol to physically contact the fatty acids and glycerides in the emulsion. Super-critical fluids have the properties of a gas and a liquid. Thus, the super-critical alcohol will be able to effuse through the other components in the emulsion like a gas. However, the super-critical alcohol will be relatively dense as compared to gaseous alcohol. As a result, the physical collision rate between the alcohol and the emulsion components will be high. Both of the foregoing characteristics will result in the alcohol readily coming into contact with the glycerides.

The ability of the super critical alcohol to physically encounter and react with the glycerides and free fatty acids in the emulsion will be significantly enhanced by the non-laminar, and preferably turbulent, flow of the emulsion through reaction lines 202. The non-laminar flow of the emulsion in combination with the super-critical alcohol results in thorough mixing and promotes a more rapid, efficient and complete reaction, facilitating completion of the reaction in a single pass through reactor 200.

In the preferred embodiment, one or more back pressure control valves 350 are provided in manifold 207. The back pressure control valve 350 should be set at about 2500 psig. Essentially, back pressure control valve 350 will check the flow through reactor 200 if the pressure should fall below 2500 psig. This will cause the pressure to build until back pressure control valve 350 opens, allowing flow through reactor 200 to resume. It will be appreciated that back pressure control valve 350 will control for the pressure drop across reaction lines 202. This will maintain the pressure within reaction lines 202 at a sufficient level to keep the alcohols in the emulsion in a super-critical state.

At the preferred pressure and temperature, as noted above, the water in the emulsion is sub-critical, meaning above its atmospheric boiling point and below its critical point, but under sufficient pressure to prevent the water from vaporizing. Several things happen to such high temperature water. The water molecules become less polar, making the water a much more effective organic solvent. Because of the decrease in polarity and also because of the elevated temperature, many oils, including the glycerides and fatty acids in the feed stock, become soluble in water under these conditions.

Water at very high pressure and temperature also includes several orders of magnitude more hydronium ($H_3O^+$) and hydroxide ($OH^-$) ions than does water under ambient conditions. This will give the water the properties of both an acid and a base. Thus, the high temperature water can perform the role of the catalyst in breaking the glycerides into free fatty acids and glycerine. High pressure, high temperature water also inhibits the dehydration of the alcohol and glycerin. The emulsion will frequently contain dissolved impurities such as trace metals. These metals can serve as catalysts to break the alcohols into dimethyl ether, an extremely flammable gas. Similarly, the metals can serve as catalysts to break glycerin into acrolein, a highly toxic chemical. In the preferred range of temperature and pressure, the water can form ionic complexes with the metals that can inhibit the catalytic activity of trace metals, thereby preserving the alcohol and glycerin.

The waters in the emulsion are necessarily maintained at the same pressure and temperature as the alcohols and other emulsion components. These pressures and temperatures are sufficient to optimize the advantages discussed above.

Although the reaction can proceed without any water, water between the amount of about five and about twenty percent by weight of the emulsion and most preferably about ten to fifteen percent by weight of the emulsion will allow the reaction to proceed more quickly and more completely with less alcohol and fewer undesired side reactions and by-products. Water content approaching the fifteen percent range and higher complicates the isolation of alcohol from the finished product for recycling. Thus, keeping the water content of the emulsion at about ten percent by weight of the emulsion is most preferable.

There is some uncertainty as to how to characterize the water in the emulsion under the preferred conditions. On the one hand, the waters will be between the boiling point of water and the critical point of water. Such waters can be reasonably characterized as sub-critical. However, the alcohols in the emulsion will clearly be super-critical under the preferred conditions. The volume of the alcohol will be at least three to four times that of the water present. As a result, it is believed that the physical state of the alcohol predominates. Observation of the fluid during operation of reactor 200 indicates that the emulsion is behaving as a homogenous, super-critical body. This is consistent with the expected effect of a substantial quantity of super-critical alcohol in a thoroughly mixed and turbulent emulsion, namely homogenization of the entire fluid body. Thus, the entire emulsion is believed to behave like a super-critical fluid while in reactor 200.

All of the foregoing will facilitate bringing the alcohols and catalytic waters together with the glycerides and fatty acids, accelerating both the breakdown of the glycerides and fatty acids into free fatty acids and the formation of biodiesel. The reaction will proceed more quickly and less excess alcohol will be required to ensure the reaction proceeds to completion.

Overexposure to the high temperature and pressure of the reaction conditions can have adverse effects on fuel quality and viscosity. Primarily, this is the result of polymerization of polyunsaturated fatty acids from the cis form to the trans form. One way to ameliorate this risk is to operate at lower temperatures over longer periods. However, this is energy intensive and relatively expensive. A more efficient way to moderate this risk is to remove the emulsion from the reactor as soon as the reaction is substantially complete. By monitoring the state of the reaction with Coriolis mass flow meters, and utilizing manifold 207, the emulsion may be removed from reactor 200 as soon as the reaction is complete. For example, with the refined feedstock described in example no. 1, whose FOG's are primarily triglycerides, a drop in density of about 1 lb/ft$^3$ will indicate that the reaction is substantially complete.

Removing the emulsion from reactor 200 promptly upon completion of the reaction will minimize excess holding times under reaction level conditions. It will be appreciated that this is a particular concern when the quality of the feed stock is inconsistent. The amount of excess polyunsaturated fatty acids in the FOG's, particularly the amount of linoleic acid and linolenic acid, will effect how long the refined feed stock needs to be maintained under reaction conditions.

In the preferred embodiment, the emulsion should remain between about 560° and 620° F. and most preferably at about 590° F. under non-laminar, and most preferably turbulent, conditions for between about 1.5 and about 5.5 minutes and most preferably about four minutes. In the preferred embodiment, this is accomplished by passing the emulsion through about 3000 feet (915 meters) of reaction line 202 at a flow rate of about 10 feet/second (3.0 meters/second), all while maintaining the reaction lines 202, inside shells 201, in a circulating bath of 750° F. molten salt.

One potential problem for any reactive system including oils in contact with high temperature metals is coking. Carbon deposits can form from (incomplete) combustion of the oils or, in substantially oxygen free environments such as that inside reactor 200, from pyrolysis of the oils. Either process can result in the deposit of carbon on the metal surface, which can clog lines and valves and generally have a deleterious effect on the process. However, no such coking has been observed in the operation of reactor 200. It is believed that the waters in the emulsion, the homogenous super-critical nature of the fluid, and the non-laminar and preferably turbulent flow of the emulsion through reactor 200 prevent or substantially inhibit coking. In particular, it is believed that the non-laminar flow and the homogenous super-critical nature of the fluid disperse the waters evenly throughout the emulsion. This is believed to make the greater potential heat capacitance of the waters available to absorb heat from reaction line 202, thereby shielding the oils to some degree. Furthermore, to the extent that any pyrolysis does occur, the non-laminar flow is believed to scour reaction lines 202, preventing any substantial build up of coke.

Upon exiting reactor 200, the effluent will be comprised of bio-diesel, solvent (which may be bio-diesel), glycerol, alcohol, water, and contaminants. The effluent will be about 600° F. If the efficiency of the process is to be maximized, it is important that the heat from this effluent be utilized. That can be done by recycling the heat to warm the emulsion entering reactor 200 or to drive the separation of the effluent components. In the preferred embodiment, the heat of the effluent is used for both purposes.

In one embodiment, the pressure is released from the effluent stream, preferably immediately prior to or contemporaneously with entry of the effluent stream into a distillation column 300. A back pressure control valve 350, such as those available from Schubert & Salzer of Concord, N.C., is preferably used to return the effluent stream to ambient pressure. As discussed above, similar back pressure control valves 350 may be utilized at manifold 207 to maintain pressure.

It will be appreciated that upon the removal of pressure, essentially all of the alcohol and water will boil out of the 600° F. effluent stream. Most of the contaminants, including especially the organic sulfur containing contaminants, have a boiling point below 450° F. For example, some of the more common sulfur contaminants still present when effluent exits reactor 200 include disulfides and thiols, which have boiling points around 150° F. or less. Thus, most of the organic sulfur contaminants present in the effluent will boil out in first distillation column 300.

The light effluent from distillation column 300 will include the alcohol, water and contaminants. The light effluent will be passed through a second distillation column 301, where the alcohol will be boiled out, captured, and recycled for further use in bio-diesel refining. The water and remaining contaminants, most if not all of which will be water soluble, will be collected and treated, either on-site or at an off-site water treatment facility.

Suitable distillation columns 300 and 301 are available from Sulzer Chemtech of Tulsa, Okla. It will be appreciated that heat may be added to distillation columns 300 and 301 as necessary.

The heavy effluent of distillation column 300, though at atmospheric pressure, will still be at about 450° F. The heavy effluent will be passed through one or more heat exchangers 106 in order to cool the effluent to about 110° F. and to recapture the heat for use elsewhere in the process.

After passing through heat exchangers 106, the heavy effluent from first distillation column 300 will be transferred to a settling tank 400. At this stage, the effluent will comprise primarily bio-diesel (and solvent) and glycerol. Glycerol is heavier than and not miscible in bio-diesel. With time, the phases will gravity separate. Most of the remaining high boiling point contaminants are more soluble in the glycerin phase and, accordingly, will predominate in the glycerin layer. After separation, each phase may be pumped off—the glycerol for sale/disposal and the bio-diesel for further treatment, as needed. Residency in settling tank 400 on the order of twenty-four hours is expected to be sufficient to effect a substantially complete separation of bio-diesel from the glycerol.

Separation of the bio-diesel from the glycerol may be accelerated by using a centrifuge 500, such as the disc centrifuge available from Alfa Laval, of Richmond, Va.

After the bio-diesel has been removed from the glycerol, the sulfur content in the bio-diesel will be on the order of 20 to 40 ppm. This can be contrasted with sulfur levels on the order of 1000 ppm in the feedstock. It will also be appreciated that most water soluble sulfur contaminants that might have been present in the effluent from reactor 200 will have been removed either with the light effluent from distillation column 300 or with the glycerol phase in separation. The majority of any remaining sulfur contaminants are likely to be water miscible polar compounds such as alkyl sulfates.

By passing the bio-diesel through a bed of adsorbent, such as aluminum silicate, the majority of any remaining sulfur contaminants may be captured. The resulting bio-diesel will have a sulfur content of between 0 and 10 ppm, and well below 15 ppm in any event.

The bio-diesel may also be passed through a molecular sieve 600 such as those available from W.R. Grace of Baltimore, Md. to remove any residual water. This is essentially an insurance step, as distillation will have already removed substantially all waters.

The bio-diesel is passed through a one micron filter 700, such as those available from AWC, Inc. of Mobile, Ala. This ensures that the final fuel product contains substantially no particulates, or at least substantially nothing above a micron in size.

If bio-diesel is used as the solvent, there is no need to extract it from the finished product. If diesel is used as the solvent, it may or may not be necessary to remove the diesel, depending upon the intended use of the end product. If diesel or another solvent needs to be removed, separation can be accomplished by cooling the bio-diesel/solvent mixture to a temperature approaching the gel point of the bio-diesel. The gel point of fuel produced by the current process will vary depending upon the fatty acid composition of the feed stock. However, the gel point of most bio-diesel created using the process described herein will be between 15° and 65° F. By comparison, the gel point of number two diesel is around −10° F. to 20° F. As the bio-diesel and solvent mixture approaches temperatures near the gel point of the bio-diesel—commonly in the range of 65° to 60° F.—the specific gravity of the bio-diesel will increase, and the bio-diesel will sink to the bottom of the tank. This will allow the solvent to be pumped off for reuse. The bio-diesel can be warmed or simply allowed to return to ambient temperature, and its liquid properties will return. At this point the bio-diesel is ready for sale or use.

In operation, the foregoing process will yield bio-diesel having less than 15 ppm sulfur, essentially no water and will meet or exceed industry fuel specification ASTM 6751-12. This may be obtained using no more than about twenty-one percent alcohol by weight and typically alcohol quantities more on the order of about twelve to sixteen percent by weight. Total reaction time, from emulsification of the refined stock, solvent, and alcohol through post-reaction distillation will take about 4.5 minutes.

It will be appreciated that the foregoing process may be operated on a continuous, as opposed to a batch, basis. This will enhance efficiency significantly. In addition to simply allowing more bio-diesel to be produced per unit time, the continuous process makes it possible to efficiently capture and reuse heat. This, in turn, will make the cost of operation significantly less expensive.

Example No. 1

A refined feedstock was treated according to the methods described herein. The feedstock comprised about 50.7 percent by weight triolein (a symmetrical triglyceride typically present in olive oil); about 13.9 percent by weight solvent in the form of methyl oleate (bio-diesel); about 8.0 percent water by weight; about 0.0073 percent by weight carbon disulfide and 0.0073 sodium sulfate. To this was added, about 27.3 percent by weight methanol to form an emulsion. All percentages are given with respect to the emulsion. The molar ratio of the methanol to triglycerides in the emulsion was about 15:1.

The emulsion was pressurized to about 2500 psig and heated to about 600° F. It was then passed through a reactor substantially as described above. Heat transfer media in the reactor was maintained at about 750° F. Pressure in the reaction lines was maintained at about 2500 psig throughout the process.

The manifold was used to break the reaction lines in the reactor into two separate circuits, each circuit comprising seven reaction line coils and containing about 350 feet of reaction line in each circuit. The emulsion was separated into two streams, each of which was pumped through one of the circuits at about 3.0 gallons per minute. The emulsion remained in the reactor for about 4.5 minutes.

Post-reaction, the effluent comprised about 21.8 percent by weight methanol; about 64.9 percent by weight methyl oleate (about 51% by weight was formed in the reactor and about 13.9% was carry-over solvent); about 5.3 percent by weight glycerol; about 8.0 percent by weight water; about 0.0073 percent by weight carbon disulfide and about 0.0073 percent by weight sodium sulfate. The effluent was subjected to flash distillation to remove the methanol, water and carbon disulfide; centrifugation to remove the glycerol; and filtration to remove the sodium sulfate. The resultant bio-diesel (methyl oleate) met the ASTM 6751-12 fuel quality specifications for B100. Detailed results of this testing are reported in FIG. 6A.

Example No. 2

A refined feedstock was treated according to the methods described herein. The feedstock comprised about 10.3 percent by weight triolein (triglyceride); about 20.8 percent by weight diolein (diglyceride); about 10.8 percent by weight monoolein (monoglyceride); about 21.9 percent by weight solvent in the form of methyl oleate (bio-diesel); about 13.2 percent water by weight; about 0.011 percent by weight carbon disulfide and about 0.011 sodium sulfate. To this was added, about 23.0 percent by weight methanol to form an emulsion. All percentages are given with respect to the emulsion. The molar ratio of the methanol to glycerides in the emulsion was about 10:1.

The emulsion was pressurized to about 2500 psig and heated to about 600° F. It was then passed through a reactor substantially as described above. Heat transfer media in the reactor was maintained at about 750° F. Pressure in the reaction lines was maintained at about 2500 psig throughout the process.

The manifold was used to break the reaction lines in the reactor into two separate circuits, each circuit comprising seven reaction line coils and containing about 350 feet of reaction line in each circuit. The emulsion was separated into two streams, each of which was pumped through one of the circuits at about 3.25 gallons per minute. The emulsion remained in the reactor for about 4.2 minutes.

Post-reaction, the effluent comprised about 18.7 percent by weight methanol; about 61.2 percent by weight methyl oleate (about 40% by weight was formed in the reactor and about 21% was carry-over solvent); about 6.9 percent by weight glycerol; about 13.2 percent by weight water; about 0.011 percent by weight carbon disulfide and about 0.011 percent by weight sodium sulfate. The effluent was subjected to flash distillation to remove the methanol, water and carbon disulfide; centrifugation to remove the glycerol; and filtration to remove the sodium sulfate. The resultant bio-diesel (methyl oleate) met the ASTM 6751-12 fuel quality specifications for B100. Detailed results of this testing are reported in 6B.

Example No. 3

A refined feedstock was treated according to the methods described herein. The feedstock comprised about 6.2 percent by weight triolein (triglyceride); about 14.7 percent by weight diolein (diglyceride); about 21.6 percent by weight monoolein (monoglyceride); about 22 percent by weight solvent in the form of methyl oleate (bio-diesel); about 13.2 percent water by weight; about 0.011 percent by weight carbon disulfide and about 0.011 sodium sulfate. To this was added, about 22.2 percent by weight methanol to form an emulsion. All percentages are given with respect to the emulsion. The molar ratio of the methanol to glycerides in the emulsion was about 8:1.

The emulsion was pressurized to about 2500 psig and heated to about 600° F. It was then passed through a reactor substantially as described above. Heat transfer media in the reactor was maintained at about 750° F. Pressure in the reaction lines was maintained at about 2500 psig throughout the process.

The manifold was used to break the reaction lines in the reactor into two separate circuits, each circuit comprising seven reaction line coils and containing about 350 feet of reaction line in each circuit. The emulsion was separated into two streams, each of which was pumped through one of the circuits at about 3.25 gallons per minute. The emulsion remained in the reactor for about 4.2 minutes.

Post-reaction, the effluent comprised about 18.1 percent by weight methanol; about 60.3 percent by weight methyl oleate (about 38.3% by weight was formed in the reactor and about 22% was carry-over solvent); about 8.4 percent by weight glycerol; about 13.2 percent by weight water; about 0.011 percent by weight carbon disulfide and about 0.011 percent by weight sodium sulfate. The effluent was subjected to flash distillation to remove the methanol, water and carbon disulfide; centrifugation to remove the glycerol; and filtration to remove the sodium sulfate. The resultant bio-diesel (methyl oleate) met the ASTM 6751-12 fuel quality specifications for B100. Detailed results of this testing are reported in FIG. 6C.

Example No. 4

A refined feedstock was treated according to the methods described herein. The feedstock comprised about 2.0 percent by weight triolein (triglyceride); about 10.3 percent by weight diolein (diglyceride); about 10.6 percent by weight monoolein (monoglyceride); about 17.9 percent oleic acid (free fatty acid); about 24.2 percent by weight solvent in the form of methyl oleate (bio-diesel); about 14.4 percent water by weight; about 0.013 percent by weight carbon disulfide and about 0.013 sodium sulfate. To this was added, about 20.5 percent by weight methanol to form an emulsion. All percentages are given with respect to the emulsion. The molar ratio of the methanol to glycerides/free fatty acids in the emulsion was about 6:1.

The emulsion was pressurized to about 2500 psig and heated to about 600° F. It was then passed through a reactor substantially as described above. Heat transfer media in the reactor was maintained at about 750° F. Pressure in the reaction lines was maintained at about 2500 psig throughout the process.

The manifold was used to break the reaction lines in the reactor into two separate circuits, each circuit comprising seven reaction line coils and containing about 350 feet of reaction line in each circuit. The emulsion was separated into two streams, each of which was pumped through one of the circuits at about 3.25 gallons per minute. The emulsion remained in the reactor for about 4.2 minutes.

Post-reaction, the effluent comprised about 16.2 percent by weight methanol; about 63.7 percent by weight methyl oleate (about 39.7% by weight was formed in the reactor and about 24% was carry-over solvent); about 4.5 percent by weight glycerol; about 15.6 percent by weight water; about 0.013 percent by weight carbon disulfide and about 0.013 percent by weight sodium sulfate. The effluent was subjected to flash distillation to remove the methanol, water and carbon disulfide; centrifugation to remove the glycerol; and filtration to remove the sodium sulfate. The resultant bio-diesel (methyl oleate) met the ASTM 6751-12 fuel quality specifications for B100. Detailed results of this testing are reported in FIG. 6D.

Example No. 5

A refined feedstock was treated according to the methods described herein. The feedstock comprised about 9.0 percent by weight triolein (triglyceride); about 35.5 percent oleic acid (free fatty acid); about 27 percent by weight solvent in the form of methyl oleate (bio-diesel); about 15.8 percent water by weight; about 0.014 percent by weight carbon disulfide and about 0.014 sodium sulfate. To this was added, about 12.5 percent by weight methanol to form an emulsion. All percentages are given with respect to the emulsion. The molar ratio of the methanol to glycerides/free fatty acids in the emulsion was about 3:1.

The emulsion was pressurized to about 2500 psig and heated to about 600° F. It was then passed through a reactor substantially as described above. Heat transfer media in the reactor was maintained at about 750° F. Pressure in the reaction lines was maintained at about 2500 psig throughout the process.

The manifold was used to break the reaction lines in the reactor into two separate circuits, each circuit comprising seven reaction line coils and containing about 350 feet of reaction line in each circuit. The emulsion was separated into two streams, each of which was pumped through one of the circuits at about 3.5 gallons per minute. The emulsion remained in the reactor for about 3.9 minutes.

Post-reaction, the effluent comprised about 7.5 percent by weight methanol; about 73.5 percent by weight methyl oleate (about 46.5% by weight was formed in the reactor and about 27% was carry-over solvent); about 0.95 percent by weight glycerol; about 18 percent by weight water; about 0.014 percent by weight carbon disulfide and about 0.014 percent by weight sodium sulfate. The effluent was subjected to flash distillation to remove the methanol, water and carbon disulfide; centrifugation to remove the glycerol; and filtration to remove the sodium sulfate. The resultant bio-diesel (methyl oleate) met the ASTM 6751-12 fuel quality specifications for B100. Detailed results of this testing are reported in FIG. 6E.

Although the preferred embodiment has been described, those skilled in the art to which the present invention pertains will appreciate that modifications, changes, and improvements may be made without departing from the spirit of the invention defined by the following claims.

We claim:
1. A reactor comprising:
a substantially fluid tight tank comprising an interior and an exterior;
a heat transfer media positioned within said tank;
at least one reaction line positioned within said tank, wherein said reaction line is in thermal communication with said heat transfer media and wherein said reaction line is in fluid communication with said exterior of said tank;
at least one heater in thermal communication with said heat transfer media;
at least one pump configured to drive reactant fluids through said at least one reaction line; and
at least one shell positioned within said tank and substantially surrounded by said heat transfer media, wherein said at least one reaction line is positioned within said at least one shell, and wherein said at least one reaction line is configured to maintain substantially non-laminar flow of said reactant fluids.

2. A reactor according to claim 1 further comprising at least one heat exchanger in thermal communication with said reactant fluids, whereby said fluids may be heated to a desired temperature prior to entering said reaction line.

3. A reactor according to claim 2 wherein said at least one pump is configured to pressurize said reactant fluids to a desired pressure prior to entering said reaction line.

4. A reactor according to claim 3 wherein said reaction line is configured to maintain said reactant fluids at about said desired pressure.

5. A reactor according to claim 4 where said at least one reaction line is in fluid communication with at least one back pressure valve.

6. A reactor according to claim 1 wherein said at least one reaction line has a spiral configuration.

7. A reactor according to claim 2 further comprising a reservoir in fluid communication with said tank, wherein said reservoir contains an excess of said heat transfer media.

8. A reactor according to claim 7 wherein said reservoir is at least about twenty-five percent the volume of said tank.

9. A reactor according to claim 7 further comprising at least one circulation pump, said at least one circulation pump configured to mix said heat transfer media within said tank and said reservoir, whereby said heat transfer media in said tank and said reservoir may be maintained at about the same temperature.

10. A reactor according to claim 7 wherein said at least one heat exchanger is positioned in said reservoir.

11. A reactor according to claim 10 wherein said at least one heat exchanger is substantially surrounded by said heat transfer media.

12. A reactor according to claim 11 wherein said heat transfer media comprises molten salt.

13. A reactor according to claim 12 wherein said heat transfer media is selected from the group consisting of potassium nitrate, sodium nitrite, sodium nitrate, and mixtures thereof.

14. A reactor according to claim 1 further comprising a packing material substantially filling said at least one shell, wherein said at least one reaction line is substantially surrounded by said packing material.

15. A reactor according to claim 14 wherein said packing material is selected from the group consisting of silicon carbide, sand, glass and mixtures thereof.

16. A reactor according to claim 14 wherein said heat transfer media has a thermal conductivity and wherein said packing material has a thermal conductivity and wherein said thermal conductivity of said heat transfer media is greater than the thermal conductivity of said packing material.

17. A reactor according to claim 1 wherein said at least one shell is substantially torus shaped.

18. A reactor according to claim 1 wherein said at least one shell has substantially no internal corners.

19. A reactor according to claim 1 wherein said at least one shell has substantially no internal flat surfaces.

20. A reactor according to claim 1 comprising a plurality of shells, each said shell containing at least one reaction line.

21. A reactor according to claim 20 wherein said reaction lines within said plurality of shells are in fluid communication.

22. A reactor according to claim 21 further comprising a manifold in fluid communication with said reaction lines within said plurality of shells, said manifold configured to regulate flow between and around individual shells within said plurality of shells.

23. A reactor according to claim 22 wherein said plurality of shells are substantially torus shaped.

24. A reactor according to claim 23 wherein said reaction lines are configured to maintain substantially non-laminar flow of said reactant fluids.

25. A reactor according to claim 24 wherein at least one of said reaction lines is positioned in a spiral configuration within at least one of said plurality of shells.

26. A reactor according to claim 1 wherein said at least one pump is configured to pressurize said reactant fluids to a desired pressure prior to entering said reaction line.

27. A reactor according to claim 26 wherein said at least one reaction line is configured to maintain said reactant fluids at about said desired pressure.

\* \* \* \* \*